(12) United States Patent
Ueda et al.

(10) Patent No.: US 6,369,258 B1
(45) Date of Patent: Apr. 9, 2002

(54) SILICON-CONTAINING COMPOUND AND ORGANIC ELECTROLUMINESCENCE DEVICE USING THE SAME

(75) Inventors: Masato Ueda; Isao Yahagi; Makoto Kitano, all of Ibaraki (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/033,084

(22) Filed: Mar. 2, 1998

(30) Foreign Application Priority Data

Feb. 28, 1997 (JP) .............................................. 9-046719
Nov. 28, 1997 (JP) ............................................. 9-329011

(51) Int. Cl.[7] ............................. C07F 7/08; B32B 13/04
(52) U.S. Cl. ........................ 556/487; 556/489; 428/446; 428/447
(58) Field of Search ............................ 427/5, 157, 137; 252/301.16, 301.33; 428/446, 447, 448, 457; 548/406; 556/474, 482, 486, 487, 489

(56) References Cited

U.S. PATENT DOCUMENTS 3,755,354 A * 8/1973 Holub et al.
4,778,727 A * 10/1988 Tesoro et al.

FOREIGN PATENT DOCUMENTS

| EP | 0368481 A2 | 5/1990 |
| GB | 2300196 A | 10/1996 |
| JP | 08190986 | 7/1996 |
| WO | WO 86/04063 | 7/1986 |

OTHER PUBLICATIONS

Chemical Abstracts 126:271362, Japanese Kokai Tokkyo Koho JP 09012622 A2, 1997.*
Corriu, et al., "Pentacoordinated silicon compounds. Intramolecular ring closure, site . . . of the resulting chelates", Journal of Organometallic Chemistry, 395 (1990) pp. 1–26.
Chemical Abstract, Gey, et al., "The ionization energies of . . . retrieved from STN", Int. J. Mass Spectrom. Ion Phys. (1976).
Chemical Abstracts, Horner, et al., "Oganophosphorus compounds . . . Functional groups", Phosphorus Sulfur (1984).
Chemical Abstract of JP–59–198470, "Electrostatographic Development", Nov. 10, 1984.
Chemical Abstract, Yakovlev, et al., "Some problems . . . chloromethylsilanes", Zh. Obshch. Khim (1985).
Perez, et. al., "Fine Tuning of the Properties of Organically Modified Header of Polymetalates", J. Braz. Chem. Soc. (1997), 8 (1), pp. 83–86.

* cited by examiner

Primary Examiner—James O. Wilson
Assistant Examiner—Howard V. Owens, Jr.
(74) Attorney, Agent, or Firm—Fitch, Even, Tabin & Flannery

(57) ABSTRACT

The invention provides a novel silicon-containing compound having an oxidation potential of 0.3 to 1.5 V on the basis of a standard hydrogen electrode, wherein at least one alkoxy group is bonded to a silicon atom and at least one aromatic amine group is also bonded to the silicon atom.

An organic electroluminescence device having excellent mechanical and electric contact between an electrode and an organic layer is also provided by treating the surface of an anode with using a surface-treating agent comprising the above silicon-containing compound.

17 Claims, No Drawings

SILICON-CONTAINING COMPOUND AND ORGANIC ELECTROLUMINESCENCE DEVICE USING THE SAME

BACKGROUND OF THE INVENTION

1. Field of the Invention

The present invention relates to a silicon-containing compound; a method for surface treatment of an electrode, using the silicon-containing compound; a surface-treating agent of an electrode, comprising the silicon-containing compound; and an organic electroluminescence device obtained by treating an anode with the silicon-containing compound.

2. Related Art of the Invention

Recently, many studies on electronic or photoelectronic devices using organic materials have intensively been made. However, few devices are composed only of the organic material and, in almost all of cases, a device structure is formed by laminating the organic material and inorganic material. Since such an electronic or photoelectronic device consists of many inorganic/organic interfaces, because it has a structure fabricated by laminating the organic material over the inorganic material in the device, it is important to control of the mechanical and electric characteristics of the interface to improve the device performance.

In an organic electroluminescence device, for example, an inorganic transparent conductive electrode of indium-tin oxide (hereinafter abbreviated to ITO, sometimes), tin oxide ($SnO_2$), zinc oxide (ZnO), etc. is often used as a transparent conductive electrode for transmitting light and injecting holes. The device is constructed by forming a layer of an organic hole transporting material on this transparent conductive electrode, but the interface between the transparent conductive electrode and the organic hole transporting material has the following problem. That is, an ITO electrode, $SnO_2$ electrode or ZnO electrode is used after washing the surface according to solvent washing, plasma washing, etc. and the hydroxyl group or alkoxy group is formed on the surface of the surface-washed ITO electrode, $SnO_2$ electrode or ZnO electrode, thereby hydrophilizing the electrode. Since a hydrophobic functional organic material is generally used as a hole transporting film to be formed on the transparent conductive electrode, peeling of the film arises sometimes because of poor adhesion at the interface. No problem arises when a hydrophilic functional organic molecule is further formed on this hydrophilic conductive electrode. For example, Japanese Patent Kokai Publication No. 2-267888 discloses an organic electroluminescence device obtained by forming a polysilane thin film having the hole transporting property on an ITO electrode. Since a conventional polysilane compound has only a hydrophobic group on the side chain, satisfactory adhesion is still to be obtained, necessarily.

A surface-treating agent represented by a silane coupling agent is widely used as a modifier of the interface between composite materials prepared by using organic materials in combination with inorganic materials, such as elastomer, paint, adhesives, sealant, resin coat, etc., including fiber-reinforced plastic. It becomes possible to improve the adhesion between the inorganic layer and organic layer by treating with this surface-treating agent. Since almost all of surface-treating agent, which have hitherto been used, have no electron transporting property or hole transporting property, it serves only as an electric insulator, thereby to drastically deteriorate performance as the electronic or photoelectronic device.

On the other hand, the work function of the ITO electrode, $SnO_2$ electrode or ZnO electrode hardly agrees with the ionization potential of the organic hole transporting material, and a difference in potential between the transparent conductive electrode and organic hole transporting material arises. This difference in potential becomes an potential barrier to holes in case of injecting holes from the transparent conductive electrode into the organic hole transporting material, sometimes. This potential barrier causes reduction in probability of injection of holes from the transparent conductive electrode to the organic hole transporting material, thereby lowering the injection efficiency of holes. In order to solve this problem, an attempt of vacuum deposition of metal phthalocyanine having an intermediate ionization potential between the work function of the transparent conductive electrode and the ionization potential of the organic hole transporting material in the semitransparent state has been made. However, it is pointed out that the light transmission is lowered because the metal phthalocyanine has absorption in the visible light region.

SUMMARY OF THE INVENTION

An object of the present invention is to provide a novel silicon-containing compound; a method for surface treatment of an electrode, using the silicon-containing compound wherein the mechanical/electric contact between an electrode (e.g. transparent conductive electrode, etc.) and an organic layer is improved; an surface-treating agent of an electrode, comprising the silicon-containing compound; and an organic electroluminescence device (hereinafter referred to as an "organic EL device", sometimes) having excellent mechanical and electric contact between an electrode and an organic layer, which is obtained by treating an anode with the silicon-containing compound.

The present inventors have intensively studied about a surface-treating agent having the hole transporting property so as to solve the above mechanical and electric problems of the conventional technique. As a result, the present inventors have found that the injection efficiency of holes into the organic layer and adhesion can be improved a by treating the surface of the electrode with a specific silicon-containing compound. Thus, the present invention has been accomplished.

The present invention relates to [1] a silicon-containing compound having an oxidation potential of 0.3 to 1.5 V on the basis of a standard hydrogen electrode, wherein at least one alkoxy group is bonded to a silicon atom and at least one aromatic amine group is also bonded to the silicon atom.

Furthermore, the present invention relates to [2] the silicon-containing compound according to the term [1], wherein a structural formula is represented by the general formula (1):

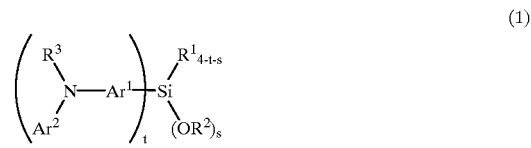

(1)

wherein $R^1$ represents a hydrogen atom, or a straight-chain or branched alkyl group having 1 to 10 carbon atoms, a cycloalkyl group having 10 carbon atoms or less, an aryl group having 6 to 24 carbon atoms or an aralkyl group having 7 to 26 carbon atoms; $R^2$ represents a straight-chain or branched alkyl group having 1 to 10 carbon atoms; $R^3$ represents a straight-chain or branched alkyl group having 1 to 10 carbon atoms, a cycloalkyl group having 10 carbon atoms or less, an aryl group having 6 to 24 carbon atoms or an aralkyl group having 7 to 26 carbon atoms; $Ar^1$ represents an arylene group having 6 to 24 carbon atoms; $Ar^2$ represents a straight-chain or branched alkyl group having 1 to 10 carbon atoms, a cycloalkyl group having 10 carbon atoms or less, an aryl group having 6 to 24 carbon atoms or an aralkyl group having 7 to 26 carbon atoms, or the general formula (2):

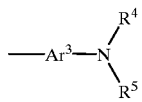

(2)

wherein $Ar^3$ represents an arylene group having 6 to 24 carbon atoms; and $R^4$ and $R^5$ independently represent a straight-chain or branched alkyl group having 1 to 10 carbon atoms, a cycloalkyl group having 10 carbon atoms or less, an aryl group having 6 to 24 carbon atoms or an aralkyl group having 7 to 26 carbon atoms; s and t independently represent an integer from 1 to 3, which satisfy the expression $2 \leq s+t \leq 4$; and a ring may be independently formed between $R^3$ and $Ar^1$, $R^3$ and $Ar^2$, or $Ar^1$ and $Ar^2$, or alternatively a ring may be independently formed between $R^4$ and $Ar^3$, or $R^4$ and $R^5$ when $Ar^2$ is represented by the general formula (2).

Also, the present invention relates to [3] a method for surface treatment of an electrode in a device having an organic layer in contact with the electrode, which comprises treating the surface of the electrode with the silicon-containing compound of the term [1] or [2] or a silicon-containing compound which has an oxidation potential of 0.3 to 1.5 V on the basis of a standard hydrogen electrode and is represented by the following general formula (3):

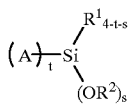

(3)

wherein $R^1$, $R^2$, s and t are the same as those defined in the general formula (1); and A represents a condensed polycyclic aromatic group having 14 to 30 carbon atoms.

Also, the present invention relates to [4] a surface-treating agent of an electrode, comprising the silicon-containing compound of the above term [1] or [2] or the silicon-containing compound represented by the general formula (3) of the term [3].

Also, the present invention relates to [5] an organic electroluminescence device comprising a pair of electrodes of an anode and a cathode, at least one of which is transparent or semitransparent, and at least one organic layer formed between the electrodes, wherein the anode is treated with the silicon-containing compound of the term [1] or [2] or the silicon-containing compound represented by the general formula (3) of the term [3].

DETAILED DESCRIPTION OF THE INVENTION

The silicon-containing compound of the present invention is characterized by a silicon-containing compound having an oxidation potential (hereinafter referred to as "Eox", sometimes) of 0.3 to 1.5 V on the basis of a standard hydrogen electrode, wherein at least one alkoxy group is bonded to a silicon atom and at least one aromatic amine group is also bonded to the silicon atom. The oxidation potential is preferably from 0.5 to 1.1 V.

Furthermore, the silicon-containing compound used as the surface-treating agent of the electrode of the present invention is characterized by the above silicon-containing compound with an aromatic amine group on the silicon atom, or a silicon-containing compound represented by the following general formula (3), wherein an oxidation potential on the basis of a standard hydrogen electrode is from 0.3 to 1.5 V. The oxidation potential is preferably from 0.5 to 1.1. As the silicon-containing compound used as the surface-treating agent of the electrode of the present invention, the above silicon-containing compound with an aromatic amine group on the silicon atom is preferable.

In the present invention, the silicon-containing compound having the oxidation potential is within this range is preferable, because holes to be injected from the electrode into the organic layer easily be injected into the organic layer via the silicon-containing compound and, therefore, the injection efficiency of holes is improved.

For example, Eox can be determined from a half-wave potential of a first oxidation wave of voltamogram obtained with an electrochemical measurement, e.g. cyclic voltammetry, etc. Specifically, cyclic voltammetry is performed by dissolving a surface-treating agent in an organic solvent containing a suitable supporting electrolyte, e.g. 0.1 N solution of tetrabutylammonium tetrafluoroborate in dichloromethane, using a pair of platinum electrodes as a working electrode and a counter electrode, and using a silver/silver chloride electrode, a saturated calomel electrode, a standard hydrogen electrode, etc. as a reference electrode. A concentration of the silicon-containing compound of the present invention may be selected so that the oxidation wave curve can be easily detected.

A lower-value voltage at the point of intersections of a straight line, which is drawn parallel to a base line at the half-height between a peak of the first oxidation wave curve and base line on the resulting cyclic voltamogram, and an oxidation wave may be taken as Eox.

In the silicon-containing compound whose structural formula is represented by the above general formula (1), the group of $R^1$ other than the hydrogen atom is a straight-chain or branched alkyl group having 1 to 10 carbon atoms, a cycloalkyl group having 10 carbon atoms or less, an aryl group having 6 to 24 carbon atoms or an aralkyl group having 7 to 26 carbon atoms, preferably a straight-chain or branched alkyl group having 1 to 10 carbon atoms.

The aryl and aralkyl groups may be substituted with a straight-chain or branched alkyl group having 1 to 6 carbon atoms or a cycloalkyl group having 6. carbon atoms or less. Specific examples of the substituent of the aryl and aralkyl groups include methyl group, ethyl group, n-propyl group, isopropyl group, n-butyl group, sec-butyl group, tert-butyl group, pentyl group, hexyl group, cyclohexyl group, etc., preferably methyl group and ethyl group.

Specific examples of $R^1$ other than the hydrogen atom include alkyl groups such as methyl group, ethyl group, n-propyl group, isopropyl group, n-butyl group, sec-butyl group, tert-butyl group, pentyl group, hexyl group, octyl group, dodecyl group, etc.; cycloalkyl groups such as cyclohexyl group, etc.; aryl groups such as phenyl group, naphthyl group, anthryl group, biphenyl group, etc.; and aralkyl groups such as benzyl group, phenethyl group, p-methylbenzyl group, etc.; preferably methyl group, ethyl group, n-propyl group, isopropyl group and n-butyl group.

In the silicon-containing compound represented by the general formula (1), $R^2$ is a straight-chain or branched alkyl group having 1 to 10 carbon atoms, preferably a straight-chain or branched alkyl group having 1 to 3 carbon atoms.

Specific examples of $R^2$ include methyl group, ethyl group, n-propyl group, isopropyl group, n-butyl group, sec-butyl group, tert-butyl group, pentyl group, hexyl group, octyl group, dodecyl group, etc., preferably methyl group and ethyl group.

In the silicon-containing compound represented by the general formula (1), $R^3$ is a straight-chain or branched alkyl group having 1 to 10 carbon atoms, a cycloalkyl group having 10 carbon atoms or less, an aryl group having 6 to 24 carbon atoms or an aralkyl group having 7 to 26 carbon atoms, preferably a phenyl group.

Specific examples of $R^3$ include alkyl groups such as methyl group, ethyl group, n-propyl group, isopropyl group, n-butyl group, sec-butyl group, tert-butyl group, pentyl group, hexyl group, octyl group, dodecyl group, etc.; cycloalkyl groups such as cyclohexyl group, etc.; aryl groups such as phenyl group, naphthyl group, anthryl group, biphenyl group, etc.; and aralkyl groups such as benzyl group, phenethyl group, p-methylbenzyl group, etc.

In the silicon-containing compound represented by the general formula (1), $Ar^1$ is an arylene group having 6 to 24 carbon atoms. Specific examples thereof include phenylene, naphthylene and biphenylene groups, preferably a phenylene group.

In the silicon-containing compound represented by the general formula (1), $Ar^2$ is a straight-chain or branched alkyl group having 1 to 10 carbon atoms, a cycloalkyl group having 10 carbon atoms or less or an aryl group having 6 to 24 carbon atoms or an aralkyl group having 7 to 26 carbon atoms, preferably an aryl group having 6 to 24 carbon atoms. Specific examples thereof include alkyl groups such as methyl group, ethyl group, n-propyl group, isopropyl group, n-butyl group, sec-butyl group, tert-butyl group, pentyl group, hexylgroup, octyl group, dodecyl group, etc.; cycloalkyl groups such as cyclohexyl group, etc.; aryl groups such as phenyl group, naphthyl group, anthryl group, biphenyl group, etc.; and aralkyl groups such as benzyl group, phenethyl group, p-methylbenzyl group, etc. Among them, a phenyl group is particularly preferable.

In the silicon-containing compound represented by the general formula (1), when $Ar^2$ is represented by the general formula (2), $R^4$ and $R^5$ independently represent a straight-chain or branched alkyl group having 1 to 10 carbon atoms, a cycloalkyl group having 10 carbon atoms or less, an aryl group having 6 to 24 carbon atoms or an aralkyl group having 7 to 26 carbon atoms, preferably an aryl group having 6 to 24 carbon atoms, particularly a phenyl group.

Specifically, $R^4$ and $R^5$ independently represent alkyl groups such as methyl group, ethyl group, n-propyl group, isopropyl group, n-butyl group, sec-butyl group, tert-butyl group, pentyl group, hexyl group, octyl group, dodecyl group, etc.; cycloalkyl groups such as cyclohexyl group, etc.; aryl groups such as phenyl group, naphthyl group, anthryl group, biphenyl group, etc.; and aralkyl groups such as benzyl group, phenethyl group, p-methylbenzyl group, etc.

In the silicon-containing compound represented by the general formula (1), when $Ar^2$ is represented by the general formula (2), an arylene group $Ar^3$ is an arylene group having 6 to 24 carbon atoms. Specific examples thereof include phenylene, naphthylene and biphenylene groups, more preferably phenylene and biphenylene groups, particularly a biphenylene group.

In $R^3$, $R^4$, $R^5$ and $Ar^2$, the alkyl and cycloalkyl groups may be substituted with a straight-chain or branched alkoxy group having 1 to 6 carbon atoms, amino group, nitro group, cyano group, ester group, halogen and the like. Specific examples of the substituent of the alkyl and cycloalkyl groups include methoxy group, ethoxy group, n-propoxy group, isopropoxy group, n-butoxy group, sec-butoxy group, tert-butoxy group, pentyloxy group, hexyloxy group, cyclohexyl group, etc., preferably methoxy group and ethoxy group.

In $R^3$, $R^4$, $R^5$, $Ar^2$, $Ar^2$ and $Ar^3$, the aryl group(e.g.the phenyl group),the aralkyl group and the arylene group (e.g.the phenylene group,the biphenylene group) may be substituted with a straight-chain or branched alkyl or alkoxy group having 1 to 6 carbon atoms, a cycloalkyl group having 6 carbon atoms or less, amino group, nitro group, cyano group, ester group, halogen and the like. Specific examples of the substituent of the aryl, aralkyl and arylene groups include methyl group, ethyl group, n-propyl group, isopropyl group, n-butyl group, sec-butyl group, tert-butyl group, pentyl group, hexyl group, methoxy group, ethoxy group, n-propoxy group, isopropoxy group, n-butoxy group, sec-butoxy group, tert-butoxy group, pentyloxy group, hexyloxy group, cyclohexyl group, etc., preferably methyl group, ethyl group, methoxy group and ethoxy group.

In the above silicon-containing compound represented by the general formula (3), A is preferably a condensed polycyclic aromatic group comprising of 3 to 8 benzene rings, more preferably a condensed polycyclic aromatic group comprising of 4 to 6 benzene rings. Specific examples of A include a pyrenyl group, a triphenylenyl group, naphthacenyl group, a perylenyl group and the like. The condensed polycyclic aromatic group having 14 to 30 carbon atoms may be substituted with a straight-chain or branched alkyl or alkoxy group having 1 to 6 carbon atoms, a cycloalkyl group having 6 carbon atoms or less, amino group, nitro group, cyano group, ester group, halogen and the like. Specific examples of the substituent of the condensed polycyclic aromatic group include methyl group, ethyl group, n-propyl group, isopropyl group, n-butyl group, sec-butyl group, tert-butyl group, pentyl group, hexyl group, methoxy group, ethoxy group, n-propoxy group, isopropoxy group, n-butoxy group, sec-butoxy group, tert-butoxy group, pentyloxy group, hexyloxy group, cyclohexyl group, etc., preferably methyl group, ethyl group, methoxy group and ethoxy group.

Specific examples of the silicon-containing compound of the present invention and silicon-containing compound used as a surface-treating agent of the electrode of the present invention are described below, but are not limited thereto. In the following formulas, $R^6$ and $R^7$ independently represent methyl group, ethyl group, n-propyl group, isopropyl group, n-butyl group, sec-butyl group, tert-butyl group, pentyl group, hexyl group, octyl group or dodecyl group; and $R^8$ to $R^{16}$ independently represent methyl group, ethyl group, n-propyl group, isopropyl group, n-butyl group, sec-butyl group, tert-butyl group, pentyl group, hexyl group, methoxy group, ethoxy group, n-propoxy group, isopropoxy group, n-butoxy group, sec-butoxy group, tert-butoxy group, pentyloxy group, hexyloxy group, cyclohexyl group, amino group, nitro group, cyano group, methyl ester group or fluorine atom. The symbol m is 0 or 1; n is an integer of 0 to 2; o is an integer of 0 to 3; p is an integer of 0 to 4; and q is an integer of 0 to 5. When hydrogen atoms of one group are substituted with two or more substituents, those substituents may be the same or different.

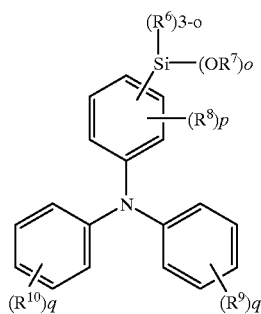
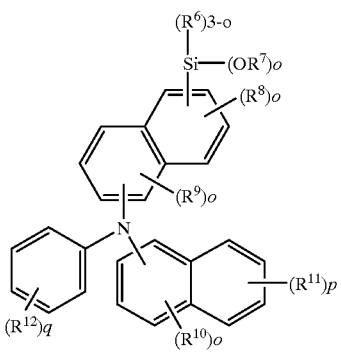
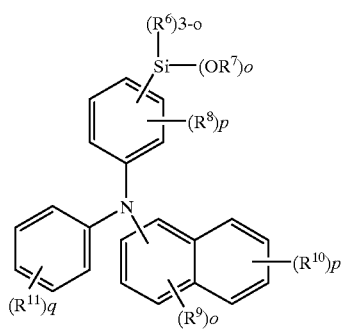
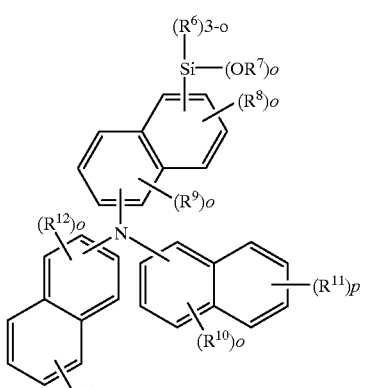
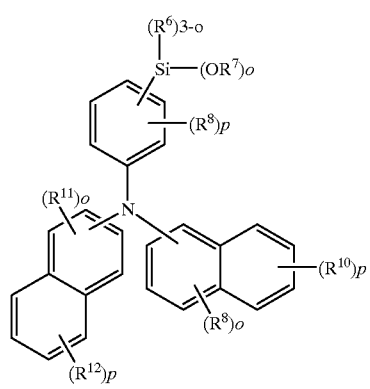
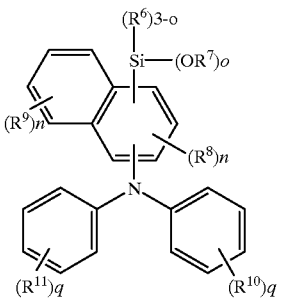
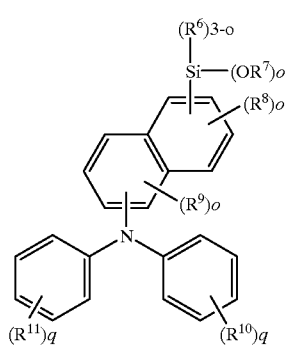
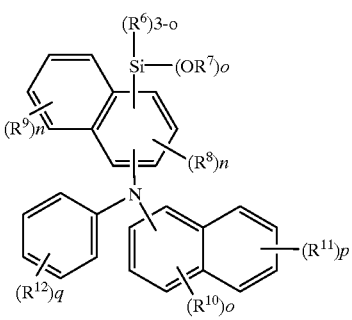

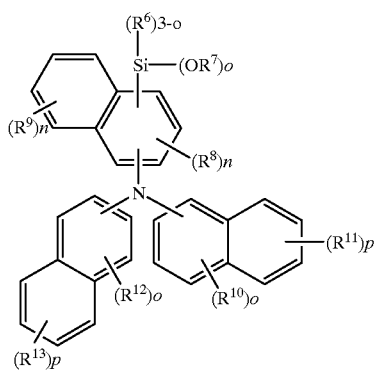
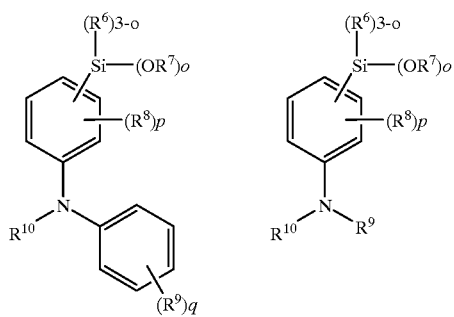
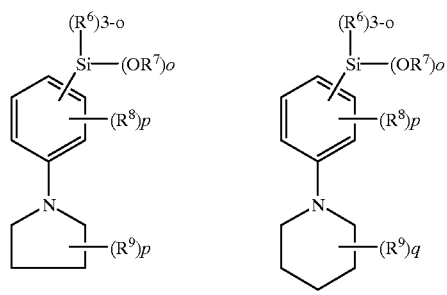
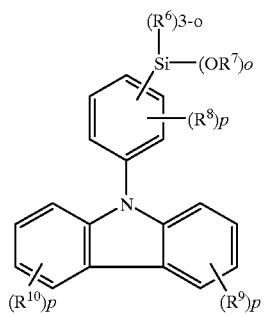
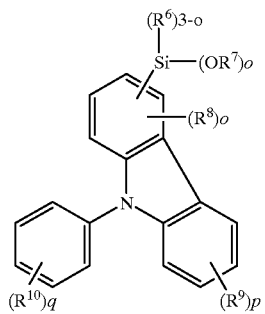
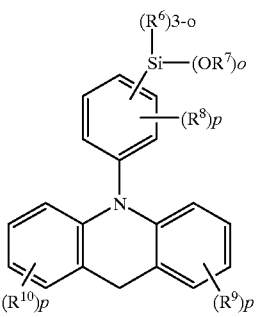
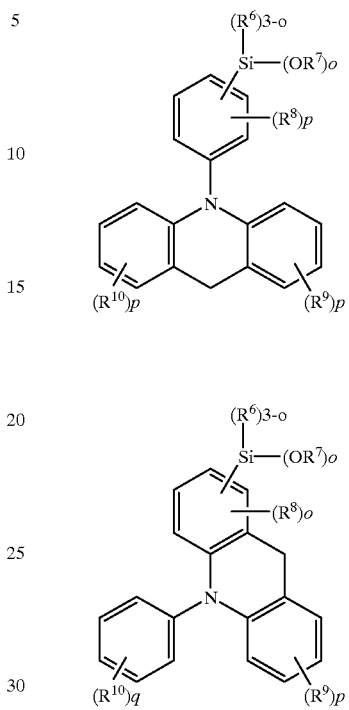
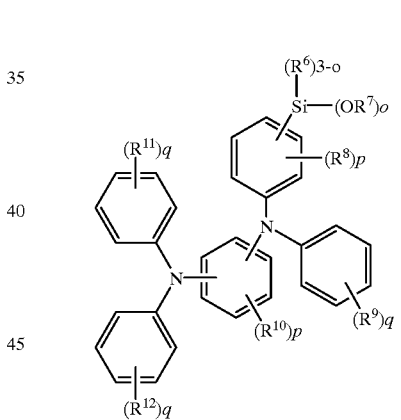
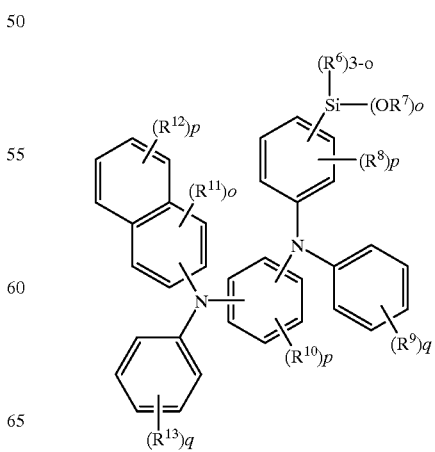

-continued
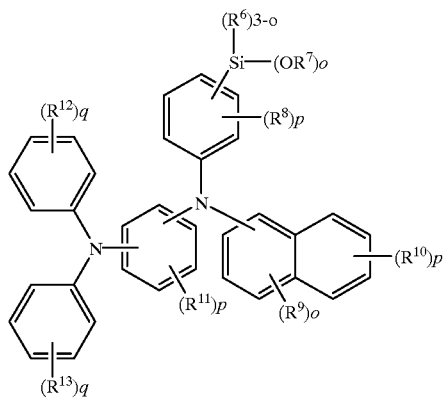
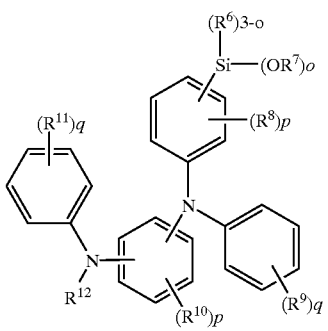
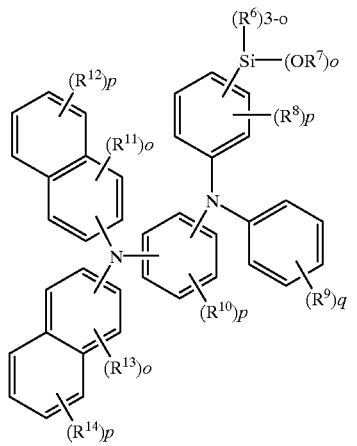
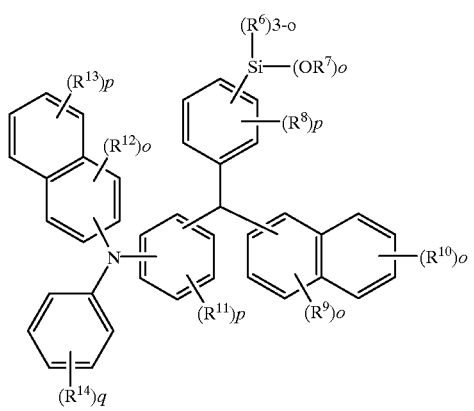
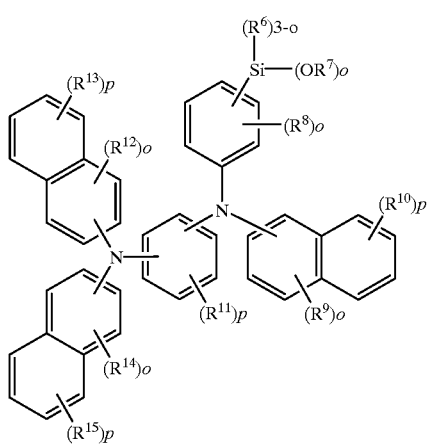

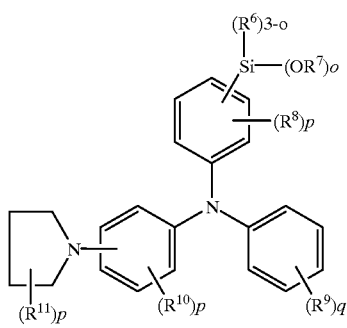
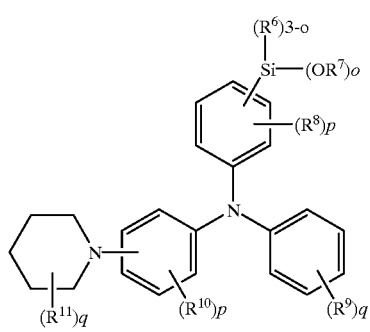
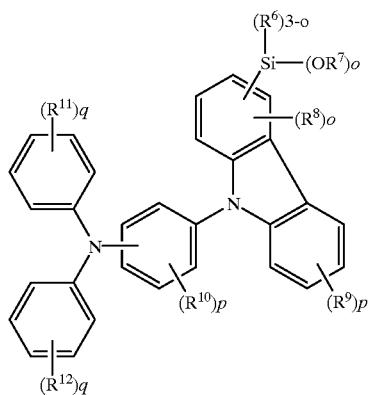
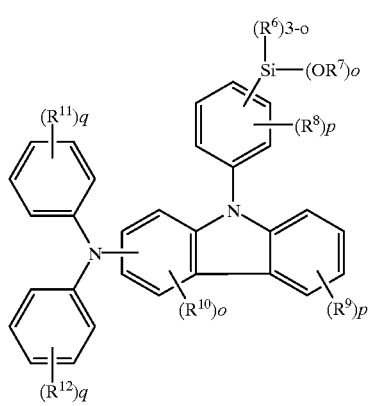
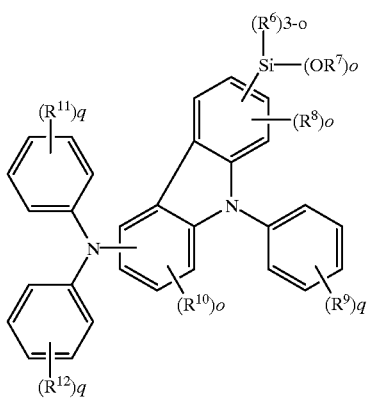
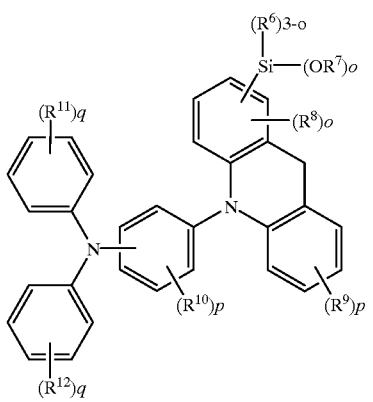
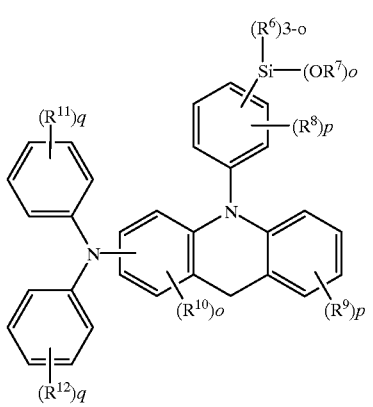
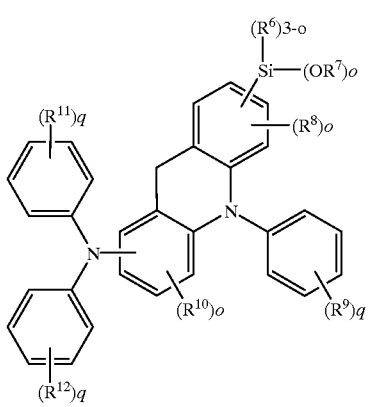

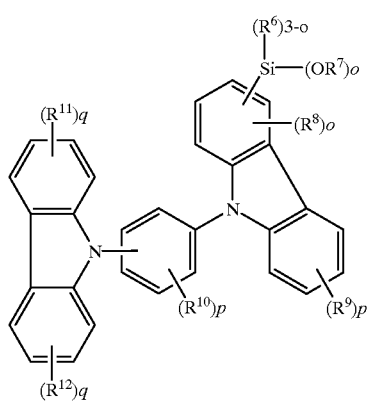
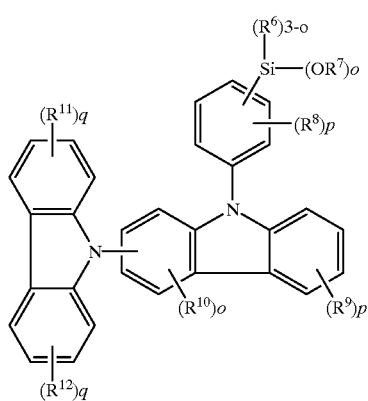
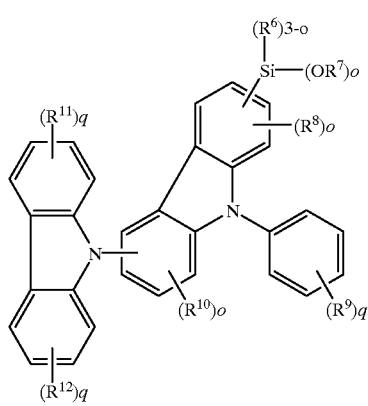
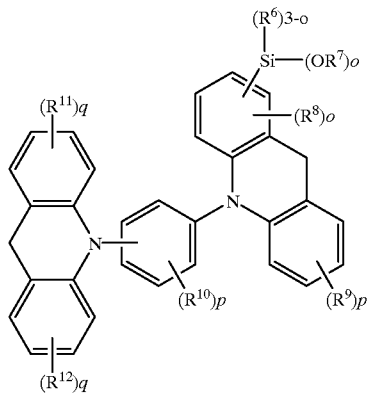
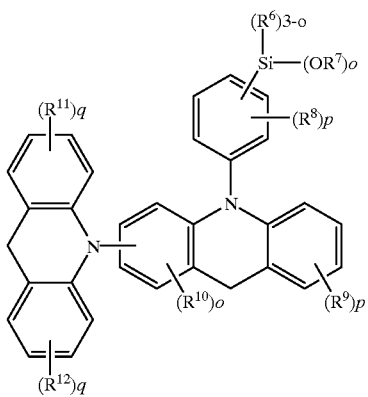
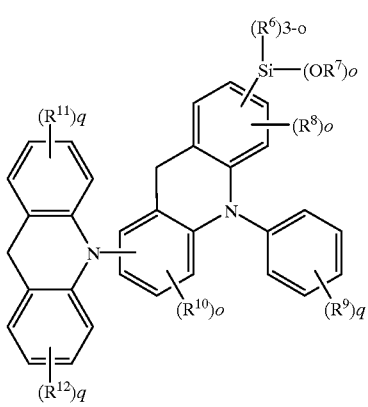
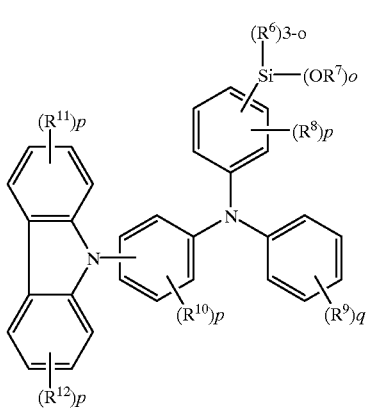
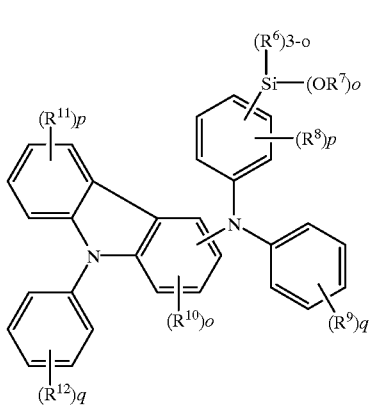

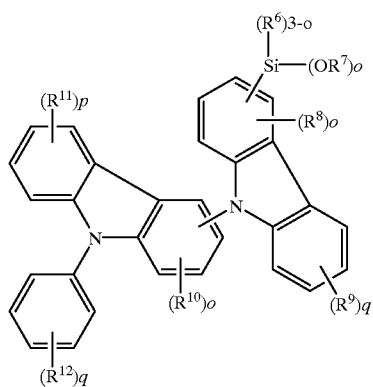
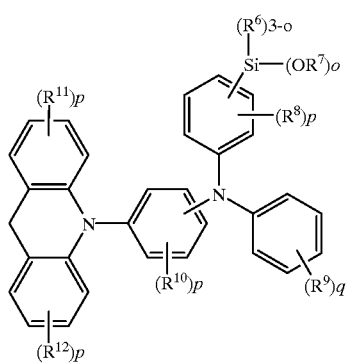
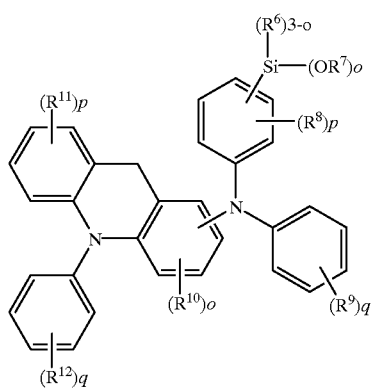
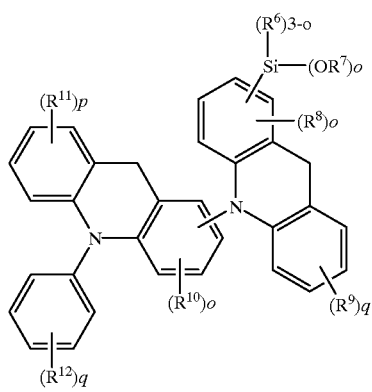
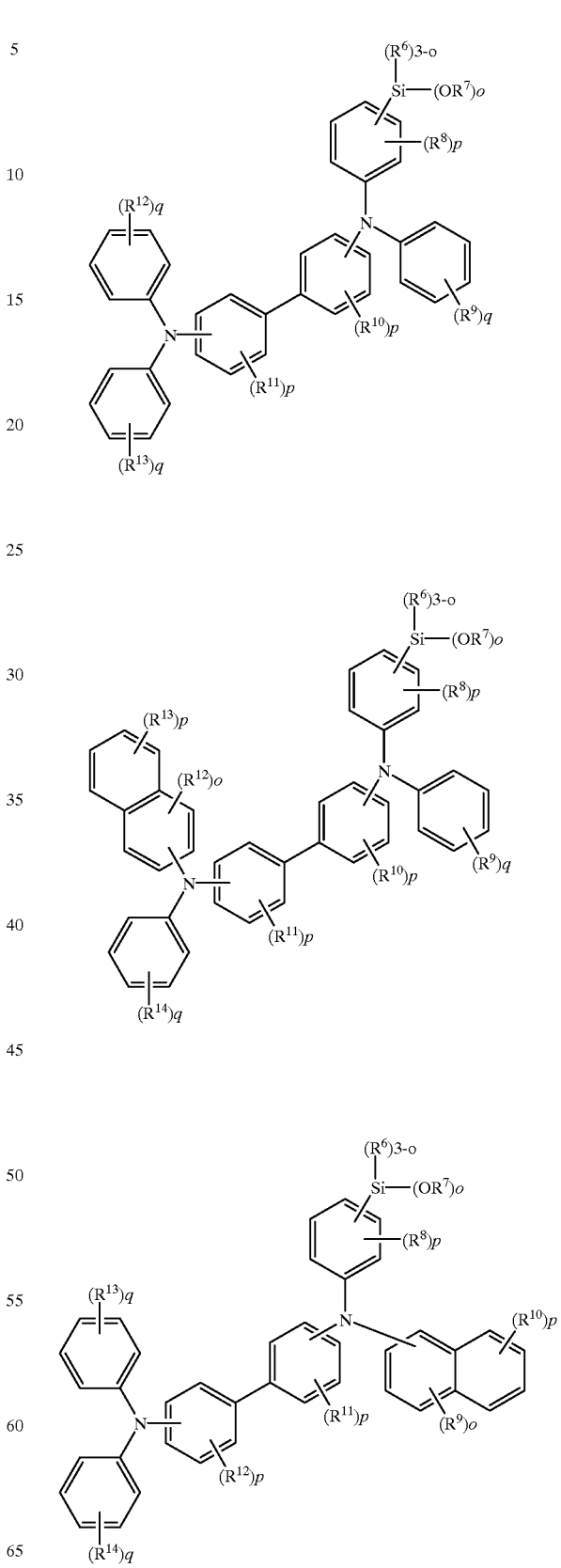

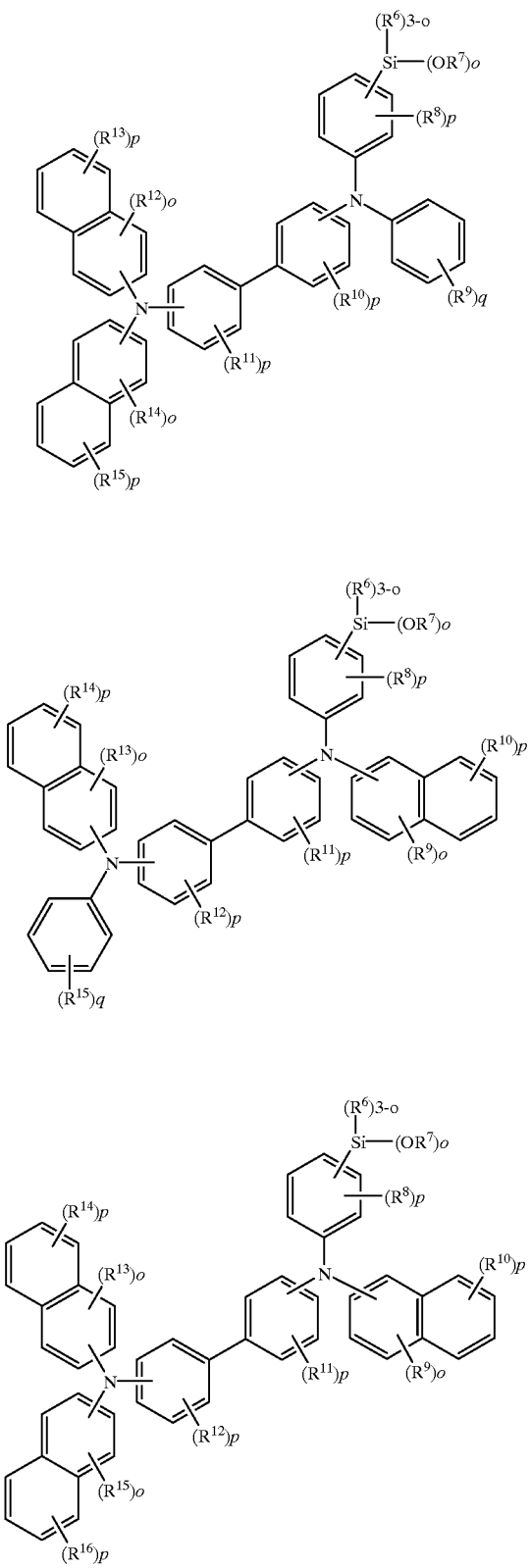
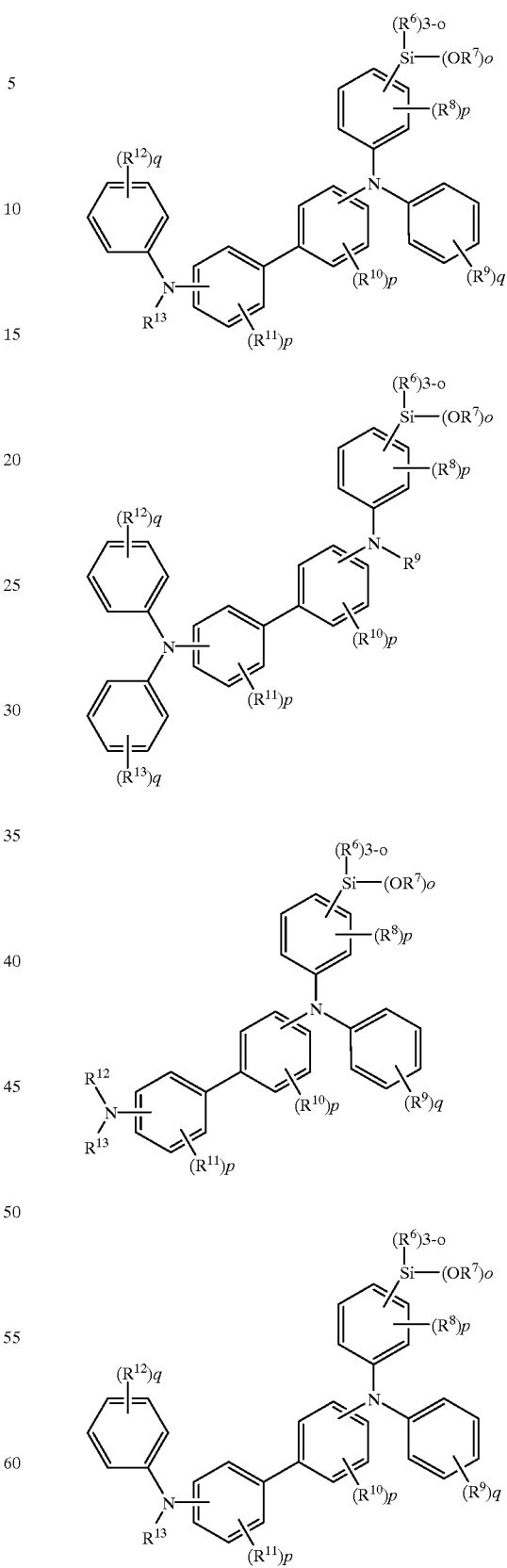

-continued
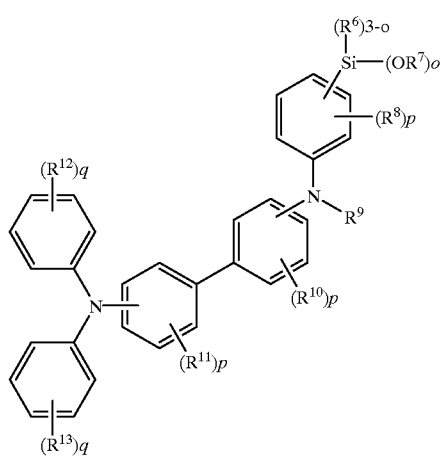
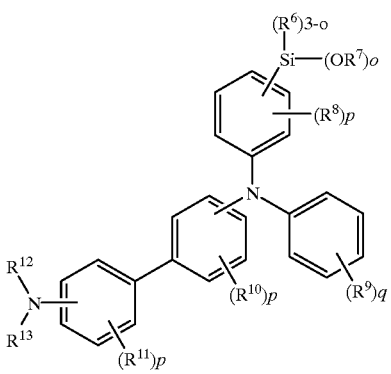
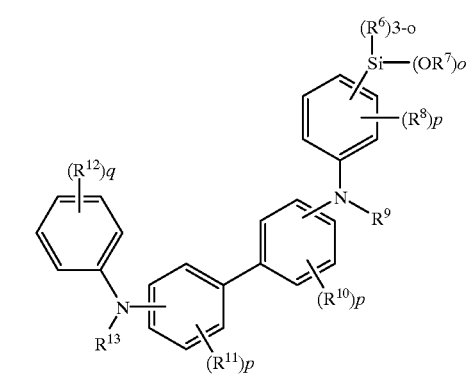
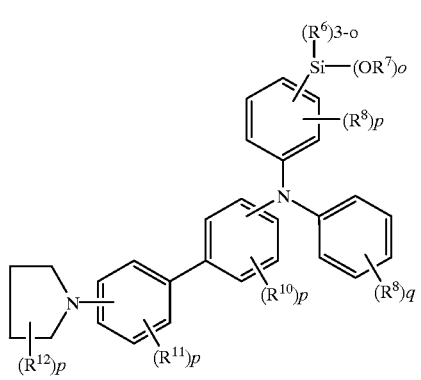
-continued
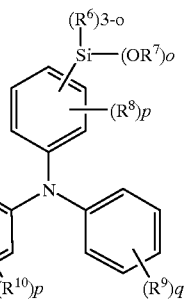
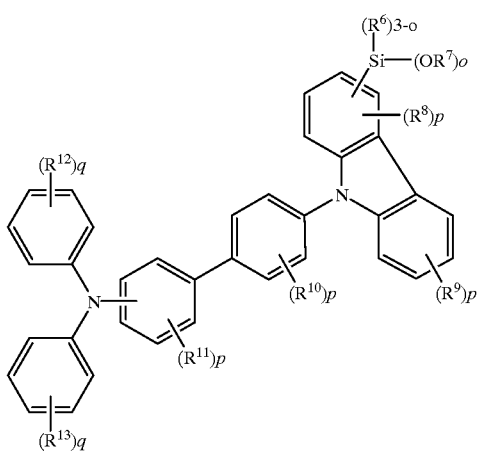
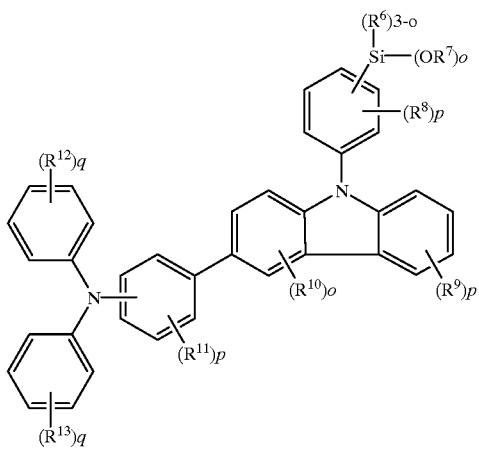
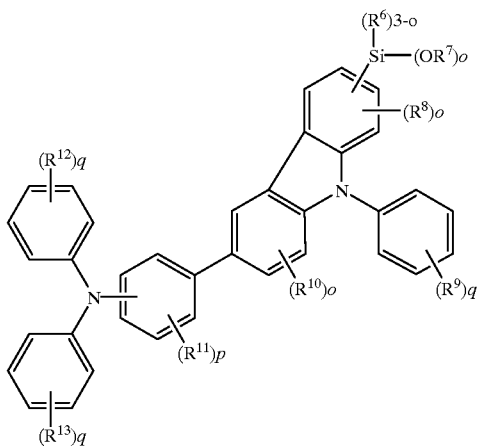

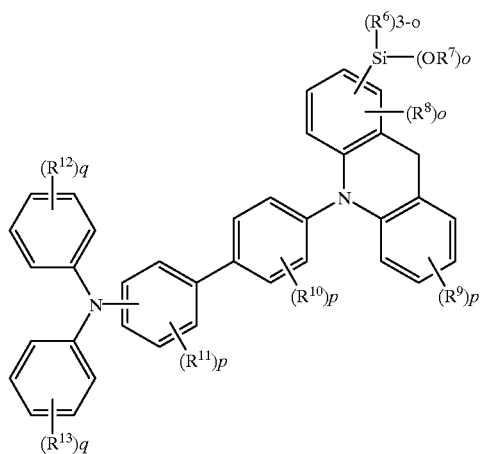
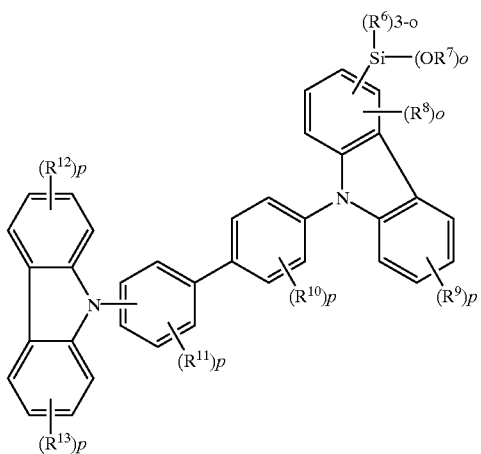
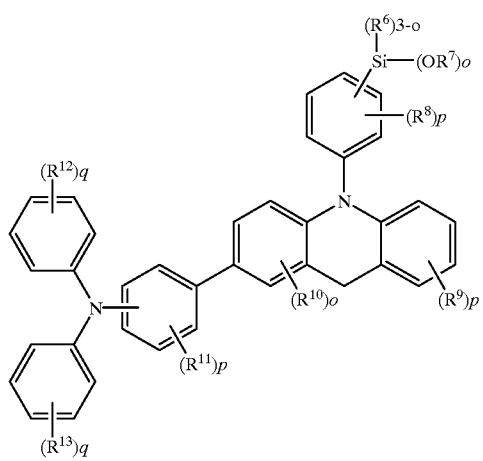
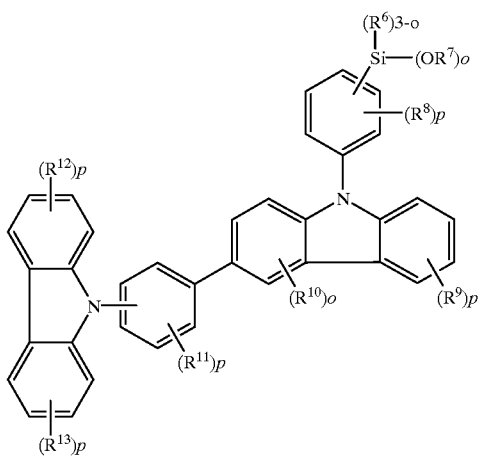
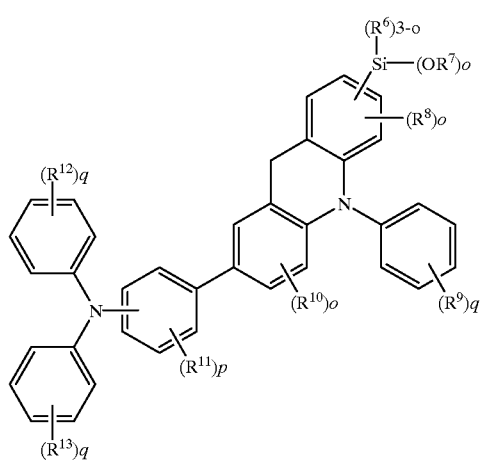
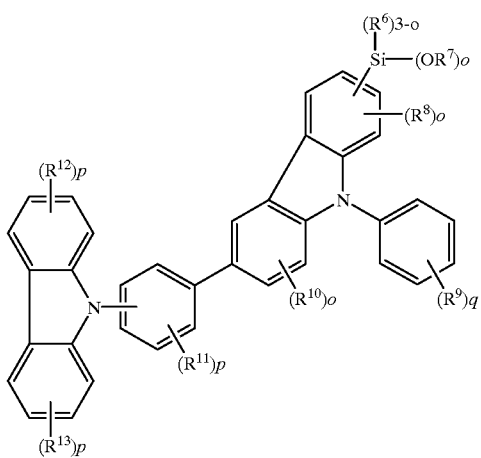

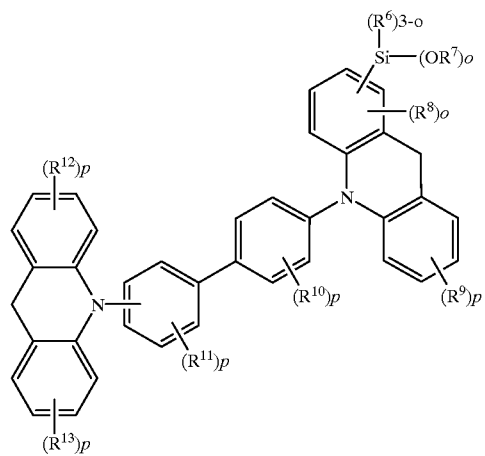
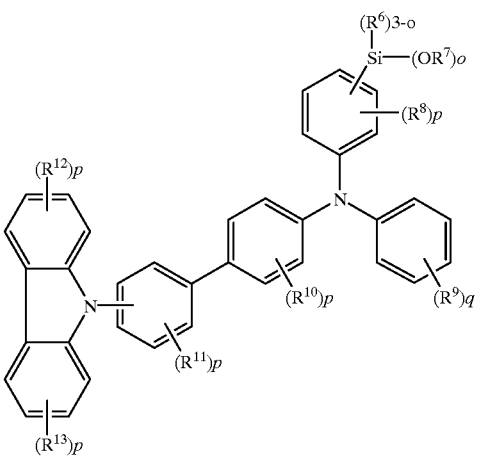
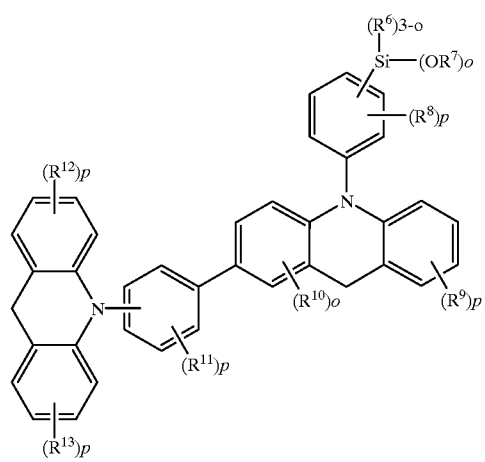
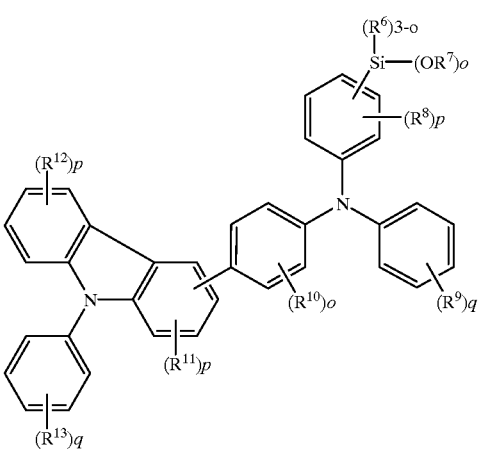
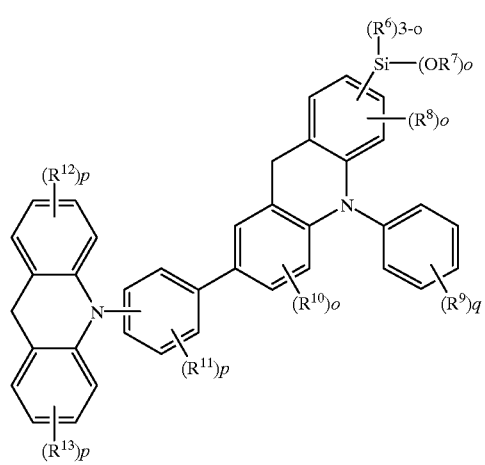
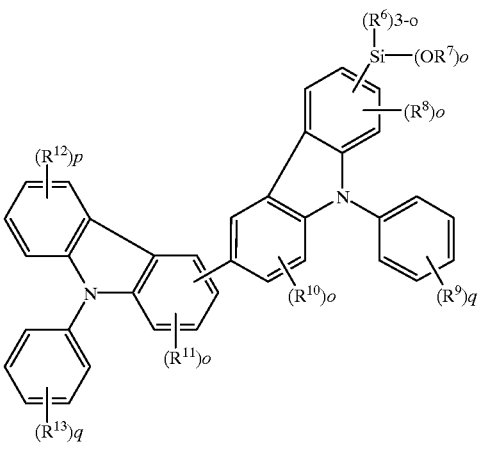

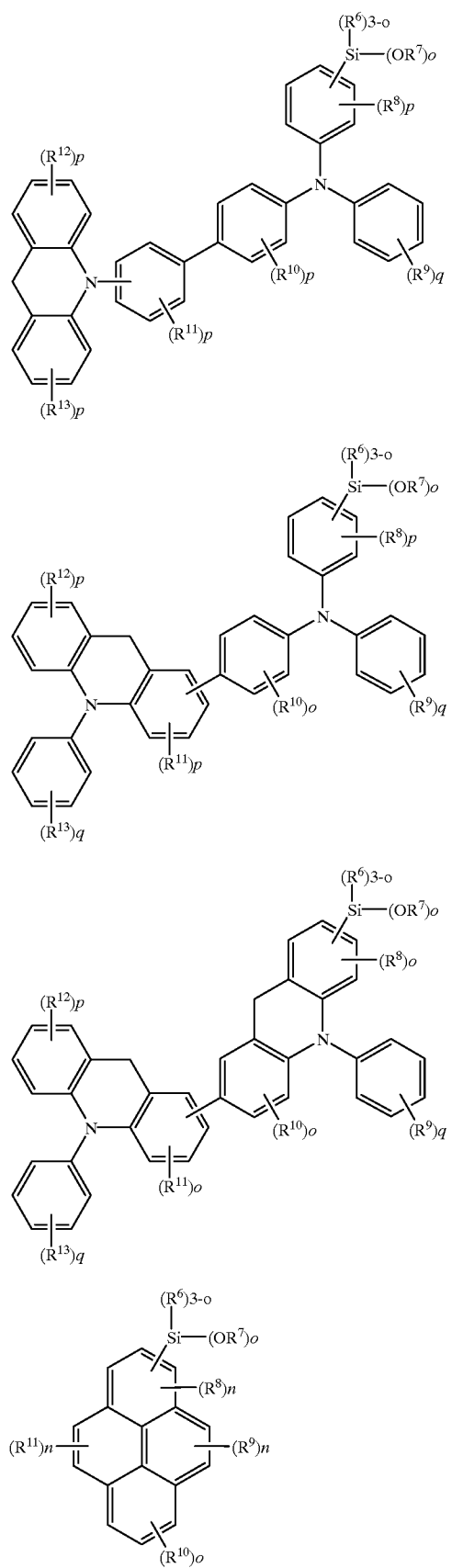
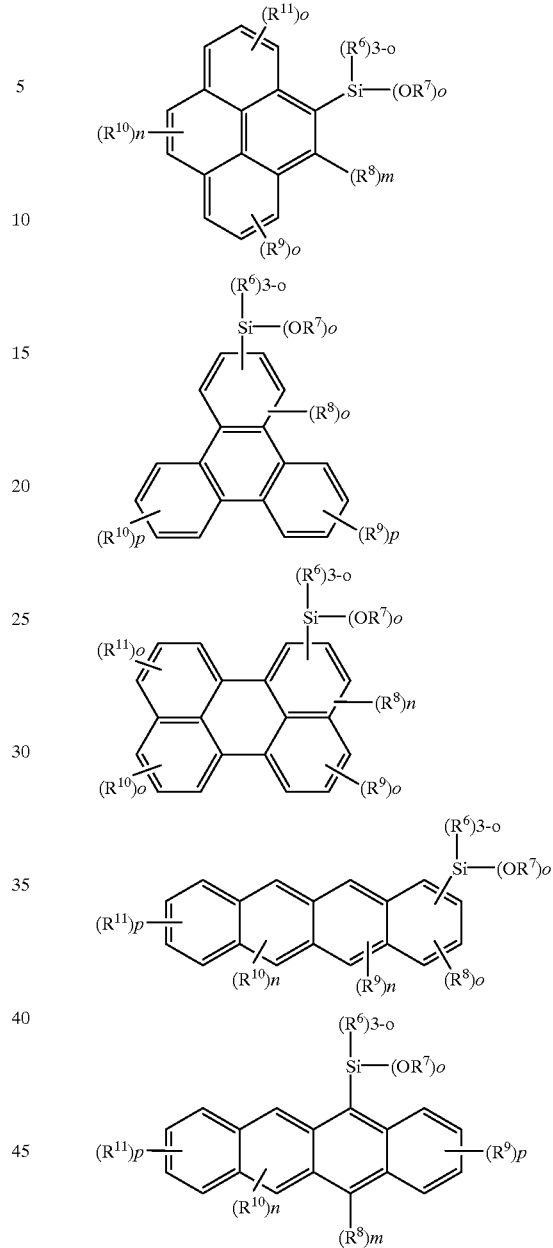

In the silicon-containing compounds represented by the general formulas (1) and (3) of the present invention, s and t may independently represent an integer from 1 to 3, which satisfy the expression $2 \leq s+t \leq 4$.

Specific examples of the silicon-containing compounds represented by the general formulas (1) and (3) in the present invention are described below, but are not limited to these compounds. N-phenyl-N-(4-triethoxy silyl phenyl)-amino benzene, N-(4-diethoxymethyl silyl phenyl)-N-phenylamino benzene, N-(4-dimethylethoxy silyl phenyl)-N-phenylamino benzene, N-phenyl-N-(4-trimethoxy silyl phenyl)-amino benzene, N-(4-dimethoxymethyl silyl phenyl)-N-phenylamino benzene, N-(4-dimethylmethoxy silyl phenyl)-N-phenylamino benzene, N-(4'-methylphenyl)-N-(4-triethoxy silyl phenyl)-amino benzene, N-(4-diethoxymethyl silyl phenyl)-N-(4'-methylphenyl)-amino benzene, N-(4-dimethylethoxy silyl phenyl )-N-(4'- methylphenyl)-amino benzene, N-(4'-methylphenyl)-N-(4-trimethoxy silyl phenyl)-amino benzene, N-(4-dimethoxymethyl silyl phenyl)-N-(4'-methylphenyl)-amino benzene, N-(4-dimethylmethoxy silyl phenyl)-N-(4'-methylphenyl)-amino benzene, N-(4"-methylphenyl)-N-(4-triethoxy silyl phenyl)-4-methyl amino benzene, N-(4'-diethoxymethyl silyl phenyl)-N-(4"-methylphenyl)-4-methyl amino benzene, N-(4'-dimethylethoxy silyl phenyl)-N-(4"-methylphenyl)-4-methyl amino benzene, N-(4"-methylphenyl)-N-(4'-trimethoxy silyl phenyl)-4-methyl amino benzene, N-(4'-dimethoxymethyl silyl phenyl)-N-(4"-methylphenyl)-4-methyl amino benzene, N-(4'-dimethylmethoxy silyl phenyl)-N-(4'-methylphenyl)-4-methyl amino benzene, N'-(4'-triethoxy silyl phenyl)-N,N,N'-triphenyl-1,4-benzene diamine, N'-(4'-diethoxymethyl silyl phenyl)-N,N,N'-triphenyl-1,4-benzene diamine, N'-(4'-dimethylethoxy silyl phenyl)-N,N,N'-triphenyl-1,4-benzene diamine, N'-(4'-trimethoxy silyl phenyl)-N,N,N'-triphenyl-1,4-benzene diamine, N'-(4'-dimethoxymethyl silyl phenyl)-N,N,N'-triphenyl-1,4-benzene diamine, N'-(4'-dimethylmethoxy silyl phenyl)-N,N,N'-triphenyl-1,4-benzene diamine, N'-(4'-triethoxy silyl phenyl)-N,N,N'-tri(4"-methylphenyl)-1,4-benzene diamine, N'-(4'-diethoxymethyl silyl phenyl)-N,N,N'-tri(4'-methylphenyl)-1,4-benzene diamine, N'-(4'-dimethylethoxy silyl phenyl)-N,N,N'-tri(4"-methylphenyl)-1,4-benzene diamine, N,N,N'-tri(4"-methylphenyl)-N'-(4'-trimethoxy silyl phenyl)-1,4-benzene diamine, N'-(4'-dimethoxymethyl silyl phenyl)-N,N,N'-tri(4"-methylphenyl)-1,4-benzene. diamine, N'-(4'-dimethylmethoxy silyl phenyl)-N,N,N'-tri(4"-methylphenyl)-1,4-benzene diamine, N,N'-di(4"-methylphenyl)-N-phenyl-N'-(4'-triethoxy silyl phenyl)-1,4-benzene diamine, N'-(4'-diethoxymethyl silyl phenyl)-N,N'-di(4"-methylphenyl)-N-phenyl-1,4-benzene diamine, N'-(4'-dimethylethoxy silyl phenyl)-N,N'-di(4"-methylphenyl)-N-phenyl-1,4-benzene diamine, N,N'-di(4"-methylphenyl)-N-phenyl-N'-(4'-trimethoxy silyl phenyl)-1,4-benzene diamine, N,N'-di(4"-methylphenyl)-N'-(4'-dimethoxymethyl silyl phenyl)-N-phenyl-1,4-benzene diamine, N'-(4'-dimethylmethoxy silyl phenyl)-N,N'-di(4"-methylphenyl)-N-phenyl-1,4-benzene diamine, N,N-di(4"-methylphenyl)-N'-phenyl-N'-(4'-triethoxy silyl phenyl)-1,4-benzene diamine, N'-(4'-diethoxymethyl silyl phenyl)-N,N-di(4"-methylphenyl)-N'-phenyl-1,4-benzene diamine, N'-(4'-dimethylethoxy silyl phenyl)-N,N-di(4"-methylphenyl)-N'-phenyl-1,4-benzene diamine, N,N-di(4"-methylphenyl)-N'-phenyl-N'-(4'-trimethoxy silyl phenyl)-1,4-benzene diamine, N,N-di(4"-methylphenyl)-N'-(4'-dimethoxymethyl silyl phenyl)-N'-phenyl-1,4-benzene diamine, N'-(4'-dimethylmethoxy silyl phenyl)-N,N-di(4"-methylphenyl)-N'-phenyl-1,4-benzene diamine, N,N-diphenyl-N'-(4"-methylphenyl)-N'-(4'-triethoxy silyl phenyl)-1,4-benzene diamine, N'-(4'-diethoxymethyl silyl phenyl)-N,N-diphenyl-N'-(4"-methylphenyl)-1,4-benzene diamine, N'-(4'-dimethylethoxy silyl phenyl)-N,N-diphenyl-N'-(4"-methylphenyl)-1,4-benzene diamine, N,N-diphenyl-N'-(4"-methylphenyl)-N'-(4'-trimethoxy silyl phenyl)-1,4-benzene diamine, N'-(4'-dimethoxymethyl silyl phenyl)-N,N-diphenyl-N'-(4"-methylphenyl)-1,4-benzene diamine, N'-(4'-dimethylmethoxy silyl phenyl)-N,N-diphenyl-N'-(4"-methylphenyl)-1,4-benzene diamine, N,N'-diphenyl-N-(4"-methylphenyl)-N'-(4'-triethoxy silyl phenyl)-1,4-benzene diamine, N'-(4'-diethoxymethyl silyl phenyl)-N,N'-diphenyl-N-(4"-methylphenyl)-1,4-benzene diamine, N'-(4'-dimethylethoxy silyl phenyl)-N,N'-diphenyl-N-(4"-methylphenyl)-1,4-benzene diamine, N,N'-diphenyl-N-(4"-methylphenyl)-N'-(4'-trimethoxy silyl phenyl)-1,4-benzene diamine, N'-(4'-dimethoxymethyl silyl phenyl)-N,N'-diphenyl-N-(4"-methylphenyl)-1,4-benzene diamine, N'-(4'-dimethylmethoxy silyl phenyl)-N,N'-diphenyl-N-(4"-methylphenyl)-1,4-benzene diamine, N'-(4'-triethoxy silyl phenyl)-N,N,N'-tri(2",4",6"-trimethylphenyl)-1,4-benzene diamine, N'-(4'-diethoxymethyl silyl phenyl)-N,N,N'-tri(2",4",6"-trimethylphenyl)-1,4-benzene diamine, N'-(4'-dimethylethoxy silyl phenyl)-N,N,N'-tri(2",4",6"-trimethylphenyl)-1,4-benzene diamine, N'-(4-trimethoxy silyl phenyl)-N,N,N'-tri(2",4",6"-trimethylphenyl)-1,4-benzene diamine, N'-(4'-dimethoxymethyl silyl phenyl)-N,N,N'-tri(2",4",6"-trimethylphenyl)-1,4-benzene diamine, N'-(4'-dimethylmethoxy silyl phenyl)-N,N,N'-tri(2",4",6"-trimethylphenyl)-1,4-benzene diamine, N,N,N'-tri(4"-ethylphenyl)-N'-(4'-triethoxy silyl phenyl)-1,4-benzene diamine, N'-(4'-diethoxymethyl silyl phenyl)-N,N,N'-tri(4"-ethylphenyl)-1,4-benzene diamine, N'-(4'-dimethylethoxy silyl phenyl)-N,N,N'-tri(4"-ethylphenyl)-1,4-benzene diamine, N,N,N'-tri(4"-ethylphenyl)-N'-(4'-trimethoxy silyl phenyl)-1,4-benzene diamine, N'-(4'-dimethoxymethyl silyl phenyl)-N,N,N'-tri(4"-ethylphenyl)-1,4-benzene diamine, N'-(4'-dimethylmethoxy silyl phenyl)-N,N,N'-tri(4"-ethylphenyl)-1,4-benzene diamine, N,N,N'-tri(3",5"-dimethylphenyl)-N'-(4'-triethoxy silyl phenyl)-1,4-benzene diamine, N'-(4'-diethoxymethyl silyl phenyl)-N,N,N'-tri(3",5"-dimethylphenyl)-1,4-benzene diamine, N'-(4'-dimethylethoxy silyl phenyl)-N,N,N'-tri(3",5"-dimethylphenyl)-1,4-benzene diamine, N,N,N'-tri(3",5"-dimethylphenyl)-N'-(4'-trimethoxy silyl phenyl)-1,4-benzene diamine, N'-(4'-dimethoxymethyl silyl phenyl)-N,N,N'-tri(3",5"-dimethylphenyl)-1,4-benzene diamine, N'-(4'-dimethylmethoxy silyl phenyl)-N,N,N'-tri(3",5"-dimethylphenyl)-1,4-benzene diamine, N'-(4'-triethoxy silyl phenyl)-N,N,N'-tri(3"-methylphenyl)-1,4-benzene diamine, N'-(4'-diethoxymethyl silyl phenyl)-N,N,N'-tri(3"-methylphenyl)-1,4-benzene diamine, N'-(4'-dimethylethoxy silyl phenyl)-N,N,N'-tri(3"-methylphenyl)-1,4-benzene diamine, N,N,N'-tri(3"-methylphenyl)-N'-(4'-trimethoxy silyl phenyl)-1,4-benzene diamine, N'-(4'-dimethoxymethyl silyl phenyl)-N,N,N'-tri(3"-methylphenyl)-1,4-benzene diamine, N'-(4'-dimethylmethoxy silyl phenyl)-N,N,N'-tri(3"-methylphenyl)-1,4-benzene diamine, N'-(4'-triethoxy silyl phenyl)-N,N,N'-tri(4"-methoxyphenyl)-1,4-benzene diamine, N'-(4'-diethoxymethyl silyl phenyl)-N,N,N'-tri(4"-methoxyphenyl)-1,4-benzene diamine, N'-(4'-dimethylethoxy silyl phenyl)-N,N,N'-tri(4"-methoxyphenyl)-1,4-benzene diamine, N,N,N'-tri(4"-methoxyphenyl)-N'-(4'-trimethoxy silyl phenyl)-1,4-benzene diamine, N'-(4'-dimethoxymethyl silyl phenyl)-N,N,N'-tri(4"-methoxyphenyl)-1,4-benzene diamine, N'-(4'-dimethylmethoxy silyl phenyl)-N,N,N'-tri(4"-methoxyphenyl)-1,4-benzene diamine, 3-methyl-N'-(4"-triethoxy silyl phenyl)-N,N,N'-triphenyl-1,4-benzene diamine, 3-methyl-N'-(4'-diethoxymethyl silyl phenyl)-N,N,N'-triphenyl-1,4-benzene diamine, 3-methyl-N'-(4'-dimethylethoxy silyl phenyl)N,N,N'-triphenyl-1,4-benzene diamine, 3-methyl-N'-(4'-trimethoxy silyl phenyl)-N,N,N'-triphenyl-1,4-benzene diamine, 3-methyl-N'-(4'-dimethoxymethyl silyl phenyl)-N,N,N'-triphenyl-1,4-benzene diamine, 3-methyl-N'-(4'-dimethylmethoxy silyl phenyl)-N,N,N'-triphenyl-1,4-benzene diaminei 3-methyl-N'-(4'-triethoxy silyl phenyl)-N,N,N'-tri(4"-methylphenyl)-1,4-benzene diamine, 3-methyl-N'-(4'-diethoxymethyl silyl phenyl)-N,N,N'-tri(4"-methylphenyl)-1,4-benzene diamine, 3-methyl-N'-(4'-dimethylethoxy silyl phenyl)-N,N,N'-tri(4"-methylphenyl)-1,4-benzene diamine, 3-methyl-N,N,N'-tri(4"-methylphenyl)-N'-(4'-trimethoxy silyl phenyl)-1,4- benzene diamine, 3-methyl-N'-(4'-dimethoxymethyl silyl phenyl)-N,N,N'-tri(4"-methylphenyl)-1,4-benzene diamine, 3-methyl-N'-(4'-dimethylmethoxy silyl phenyl)-N,N,N'-tri(4"-methylphenyl)-1,4-benzene diamine, N'-(4'-triethoxy silyl phenyl)-N,N,N'-triphenyl-1,3-benzene diamine, N'-(4'-diethoxymethyl silyl phenyl)-N,N,N'-triphenyl-1,3-benzene diamine, N'-(4'-dimethylethoxy silyl phenyl)-N,N,N'-triphenyl-1,3-benzene diamine, N'-(4'-trimethoxy silyl phenyl)-N,N,N'-triphenyl-1,3-benzene diamine, N'-(4'-dimethoxymethyl silyl phenyl)-N,N,N'-triphenyl-1,3-benzene diamine, N-(4'-dimethylmethoxy silyl phenyl)-N,N,N'-triphenyl-1,3-benzene diamine, N'-(4'-triethoxy silyl phenyl)-N,N,N'-tri(4"-methylphenyl)-1,3-benzene diamine, N'-(4'-diethoxymethyl silyl phenyl)-N,N,N'-tri(4"-methylphenyl)-1,3-benzene diamine, N'-(4'-dimethylethoxy silyl phenyl)-N,N,N'-tri(4"-methylphenyl)-1,3-benzene diamine, N,N,N'-tri(4"-methylphenyl)-N'-(4'-trimethoxy silyl phenyl)-1,3-benzene diamine, N'-(4'-dimethoxymethyl silyl phenyl)-N,N,N'-tri(4"-methylphenyl)-1,3-benzene diamine, N'-(4'-dimethylmethoxy silyl phenyl)-N,N,N'-tri(4"-methylphenyl)-1,3-benzene diamine, N'-(4"-triethoxy silyl phenyl)-N,N,N'-triphenyl-1,1'-biphenyl-4,4'-diamine, N'-(4"-diethoxymethyl silyl phenyl)-N,N,N'-triphenyl-1,1'-biphenyl-4,4'-diamine, N'-(4"-dimethylethoxy silyl phenyl)-N,N,N'-triphenyl-1,1'-biphenyl-4,4'-diamine, N'-(4"-trimethoxy silyl phenyl)-N,N,N'-triphenyl-1,1'-biphenyl-4,4'-diamine, N'-(4"-dimethoxymethyl silyl phenyl)-N,N,N'-triphenyl-1,1'-biphenyl-4,4'-diamine, N'-(4"-dimethylmethoxy silyl phenyl)-N,N,N'-triphenyl-1,1'-biphenyl-4,4'-diamine, N'-(4"-triethoxy silyl phenyl)-N,N,N'-tri(4"'-methylphenyl)-1,1'-biphenyl-4,4'-diamine, N'-(4"-diethoxymethyl silyl phenyl)-N,N,N'-tri(4"'-methylphenyl)-1,1'-biphenyl-4,4'-diamine, N'-(4"-dimethylethoxy silyl phenyl)-N,N,N'-tri(4"'-methylphenyl)-1,1'-biphenyl-4,4'-diamine, N,N,N'-tri(4"-methylphenyl)-N'-(4'-trimethoxy silyl phenyl)-1,1'-biphenyl-4,4'-diamine, N'-(4"-dimethoxymethyl silyl phenyl)-N,N,N'-tri(4"'-methylphenyl)-1,1'-biphenyl-4,4'-diamine, N'-(4"-dimethylmethoxy silyl phenyl)-N,N,N'-tri(4"'-methylphenyl)-1,1'-biphenyl-4,4'-diamine, N,N-di(4"'-methylphenyl)-N-phenyl-N'-(4"-triethoxy silyl phenyl)-1,1'-biphenyl-4,4'-diamine, N'-(4"-diethoxymethyl silyl phenyl)-N,N'-di(4"'-methylphenyl)-N-phenyl-1,1'-biphenyl-4,4'-diamine, N'-(4"-dimethylethoxy silyl phenyl)-N,N'-di(4"'-methylphenyl)-N-phenyl-1,1'-biphenyl-4,4'-diamine, N,N'-di(4"'-methylphenyl)-N-phenyl-N'-(4"-trimethoxy silyl phenyl)-1,1'-biphenyl-4,4'-diamine, N,N'-di(4"'-methylphenyl)-N'-(4"-dimethoxymethyl silyl phenyl)-N-phenyl-1,1'-biphenyl-4,4'-diamine, N'-(4"-dimethylmethoxy silyl phenyl)-N,N'-di(4"'-methylphenyl)-N-phenyl-1,1'-biphenyl-4,4'-diamine, N,N-di(4"'-methylphenyl)-N'-phenyl-N'-(4"-triethoxy silyl phenyl)-1,1'-biphenyl-4,4'-diamine, N'-(4"-diethoxymethyl silyl phenyl)-N,N-di(4"'-methylphenyl)-N'-phenyl-1,1'-biphenyl-4,4'-diamine, N'-(4"-dimethylethoxy silyl phenyl)-N,N-di(4"'-methylphenyl)-N'-phenyl-1,1'-biphenyl-4,4'-diamine, N,N-di(4"'-methylphenyl)-N'-phenyl-N'-(4"-trimethoxy silyl phenyl)-1,1'-biphenyl-4,4'-diamine, N,N-di(4"'-methylphenyl)-N'-(4"-dimethoxymethyl silyl phenyl)-N'-phenyl-1,1'-biphenyl-4,4'-diamine, N'-(4"-dimethylmethoxy silyl phenyl)-N,N-di(4"'-methylphenyl)-N'-phenyl-1,1'-biphenyl-4,4'-diamine, N,N-diphenyl-N'-(4"'-methylphenyl)-N'-(4"-triethoxy silyl phenyl)-1,1'-biphenyl-4,4'-diamine, N'-(4"-diethoxymethyl silyl phenyl)-N,N-diphenyl-N,-(4"'-methylphenyl)-1,1'-biphenyl-4,4'-diamine, N'-(4"-dimethylethoxy silyl phenyl)-N,N-diphenyl-N'-(4"'-methylphenyl)-1,1'-biphenyl-4,4'-diamine, N,N-diphenyl-N'-(4"'-methylphenyl)-N'-(4"-trimethoxy silyl phenyl)-1,1'-biphenyl-4,4'-diamine, N'-(4"-dimethoxymethyl silyl phenyl)-N,N-diphenyl-N'-(4"'-methylphenyl)-1,1'-biphenyl-4,4'-diamine, N'-(4"-dimethylmethoxy silyl phenyl)-N,N-diphenyl-N'-(4"'-methylphenyl)-1,1'-biphenyl-4,4'-diamine, N,N'-diphenyl-N-(4"'-methylphenyl)-N'-(4"-triethoxy silyl phenyl)-1,1'-biphenyl-4,4'-diamine, N'-(4"-diethoxymethyl silyl phenyl)-N,N'-diphenyl-N-(4"'-methylphenyl)-1,1'-biphenyl-4,4'-diamine, N'-(4"-dimethylethoxy silyl phenyl)-N,N'-diphenyl-N-(4"'-methylphenyl)-1,1'-biphenyl-4,4'-diamine, N,N'-diphenyl-N-(4"'-methylphenyl)-N'-(4"-trimethoxy silyl phenyl)-1,1'-biphenyl-4,4'-diamine, N'-(4"-dimethoxymethyl silyl phenyl)-N,N'-diphenyl-N-(4"'-methylphenyl)-1,1'-biphenyl-4,4=-diamine, N'-(4"-dimethylmethoxy silyl phenyl)-N,N'-diphenyl-N-(4"'-methylphenyl)-1,1'-biphenyl-4,4'-diamine, N'-(4"-triethoxy silyl phenyl)-N,N,N'-tri(2"',4"',6"'-trimethylphenyl)-1,1'-biphenyl-4,4'-diamine, N'-(4"-diethoxymethyl silyl phenyl)-N,N,N'-tri(2"',4"',6"'-trimethylphenyl)-1,1'-biphenyl-4,4'-diamine, N'-(4"-dimethylethoxy silyl phenyl)-N,N,N'-tri(2"',4"',6"'-trimethylphenyl)-1,1'-biphenyl-4,4'-diamine, N'-(4"-trimethoxy silyl phenyl)-N,N,N'-tri(2"',4"',6"'-trimethylphenyl)-1,1'-biphenyl-4,4'-diamine, N'-(4"-dimethoxymethyl silyl phenyl)-N,N,N'-tri(2"',4"',6"'-trimethylphenyl)-1,1'-biphenyl-4,4'-diamine, N'-(4"-dimethylmethoxy silyl phenyl)-N,N,N'tri(2"',4"',6"'-trimethylphenyl)-1,1'-biphenyl-4,4'-diamine, N,N,N'-tri(4"'-ethylphenyl)-N'-(4"-triethoxy silyl phenyl)-1,1'-biphenyl-4,4'-diamine, N'-(4"-diethoxymethyl silyl phenyl)-N,N,N'-tri(4"'-ethylphenyl)-1,1'-biphenyl-4,4'-diamine, N'-(4"-dimethylethoxy silyl phenyl)-N,N,N'-tri(4"'-ethylphenyl)-1,1'-biphenyl-4,4'-diamine, N,N,N'-tri(4"'-ethylphenyl)-N'-(4"-trimethoxy silyl phenyl)-1,1'-biphenyl-4,4'-diamine, N'-(4"-dimethoxymethyl silyl phenyl)-N,N,N'-tri(4"'-ethylphenyl)-1,1'-biphenyl-4,4'-diamine, N'-(4"-dimethylmethoxy silyl phenyl)-N,N,N'-tri(4"'-ethylphenyl)-1,1'-biphenyl-4,4'-diamine, N,N,N'-tri(3"',5"'-dimethylphenyl)-N'-(4"-triethoxy silyl phenyl)-1,1'-biphenyl-4,4'-diamine, N'-(4"-diethoxymethyl silyl phenyl)-N,N,N'-tri(3"',5"'-dimethylphenyl)-1,1'-biphenyl-4,4'-diamine, N'-(4"-dimethylethoxy silyl phenyl)-N,N,N'-tri(3"',5"'-dimethylphenyl)-1,1'-biphenyl-4,4'-diamine, N,N,N'-tri(3"',5"'-dimethylphenyl)-N'-(4"-trimethoxy silyl phenyl)-1,1'-biphenyl-4,4'-diamine, N'-(4"-dimethoxymethyl silyl phenyl)-N,N,N'-tri(3"',5"'-dimethylphenyl)-1,1'-biphenyl-4,4'-diamine, N'-(4"-dimethylmethoxy silyl phenyl)-N,N,N'-tri(3"',5"'-dimethylphenyl)-1,1'-biphenyl-4,4'-diamine, N'-(4"-triethoxy silyl phenyl)-N,N,N'-tri(3"'-methylphenyl)-1,1'-biphenyl-4,4'-diamine, N'-(4"-diethoxymethyl silyl phenyl)-N,N,N'-tri(3"'-methylphenyl)-1,1'-biphenyl-4,4'-diamine, N'-(4"-dimethylethoxy silyl phenyl)-N,N,N'-tri(3"'-methylphenyl)-1,1'-biphenyl-4,4'-diamine, N,N,N'-tri(3"'-methylphenyl)-N'-(4"-trimethoxy silyl phenyl)-1,1'-biphenyl-4,4'-diamine, N'-(4"-dimethoxymethyl silyl phenyl)-N,N,N'-tri(3"'-methylphenyl)-1,1'-biphenyl-4,4'-diamine, N'-(4"-dimethylmethoxy silyl phenyl)-N,N,N'-tri(3"'-methylphenyl)-1,1'-biphenyl-4,4'-diamine, N'-(4"-triethoxy silyl phenyl)-N,N,N'-tri(4"'-methoxyphenyl)-1,1'-biphenyl-4,4'-diamine, N'-(4"-diethoxymethyl silyl phenyl)-N,N,N'-tri(4"'-methoxyphenyl)-1,1'-biphenyl-4,4'-diamine, N'-(4"-dimethylethoxy silyl phenyl)-N,N,N'-tri(4"'-methoxyphenyl)-1,1'-biphenyl-4,4'-diamine, N,N,N'-tri(4"'-methoxyphenyl)-N'-(4,4"-trimethoxy silyl phenyl)-1,1'-biphenyl-4,4'-diamine, N'-(4"-dimethoxymethyl silyl phenyl)-N,N,N'-tri(4"'-methoxyphenyl)-1,1'-biphenyl-4,4'-diamine, N'-(4"-dimethylmethoxy silyl phenyl)-N,N,N'-tri(4"'-methoxyphenyl)-1,1'-biphenyl-4,4'-diamine, 3,3'- dimethyl-N'-(4"-triethoxy silyl phenyl)-N,N,N'-triphenyl-1,1'-biphenyl-4,4'-diamine, 3,3'-dimethyl-N'-(4"-diethoxymethyl silyl phenyl)-N,N,N'-triphenyl-1,1'-biphenyl-4,4'-diamine, 3,3'-dimethyl-N'-(4"-dimethylethoxy silyl phenyl)-N,N,N'-triphenyl-1,1'-biphenyl-4,4'-diamine, 3,3'-dimethyl-N'-(4"-trimethoxy silyl phenyl)-N,N,N'-triphenyl-1,1'-biphenyl-4,4'-diamine, 3,3'-dimethyl-N'-(4"-dimethoxymethyl silyl phenyl)-N,N,N'-triphenyl-1,1'-biphenyl-4,4'-diamine, 3,3'-dimethyl-N'-(4"-dimethylmethoxy silyl phenyl)-N,N,N'-triphenyl-1,1'-biphenyl-4,4'-diamine, 3,3'-dimethyl-N'-(4"-triethoxy silyl phenyl)-N,N,N'-tri(4"'-methylphenyl)-1,1'-biphenyl-4,4'-diamine, 3,3'-dimethyl-N'-(4"-diethoxymethyl silyl phenyl)-N,N,N'-tri(4"'-methylphenyl)-1,1'-biphenyl-4,4'-diamine, 3,3'-dimethyl-N'-(4"-dimethylethoxy silyl phenyl)-N,N,N'-tri(4"'-methylphenyl)-1,1'-biphenyl-4,4'-diamine, 3,3'-dimethyl-N,N,N'-tri(4"'-methylphenyl)-N'-(4"-trimethoxy silyl phenyl)-1,1'-biphenyl-4,4'-diamine, 3,3'-dimethyl-N'-(4"-dimethoxymethyl silyl phenyl)-N,N,N'-tri(4"'-methylphenyl)-1,1'-biphenyl-4,4'-diamine, 3,3'-dimethyl-N'-(4"-dimethylmethoxy silyl phenyl)-N,N,N'-tri(4"'-methylphenyl)-1,1'-biphenyl-4,4'-diamine, 2,2'-dimethyl-N'-(4"-triethoxy silyl phenyl)-N,N,N'-triphenyl-1,1'-biphenyl-4,4'-diamine, 2,2'-dimethyl-N'-(4"-diethoxymethyl silyl phenyl)-N,N,N'-triphenyl-1,1'-biphenyl-4,4'-diamine, 2,2'-dimethyl-N'-(4"-dimethylethoxy silyl phenyl)-N,N,N'-triphenyl-1,1'-biphenyl-4,4'-diamine, 2,2'-dimethyl-N'-(4"-trimethoxy silyl phenyl)-N,N,N'-triphenyl-1,1'-biphenyl-4,4'-diamine, 2,2'-dimethyl-N'-(4"-dimethoxymethyl silyl phenyl)-N,N,N'-triphenyl-1,1'-biphenyl-4,4'-diamine, 2,2'-dimethyl-N'-(4"-dimethylmethoxy silyl phenyl)-N,N,N'-triphenyl-1,1'-biphenyl-4,4'-diamine, 2,2'-dimethyl-N'-(4"-triethoxy silyl phenyl)-N,N,N'-tri(4"'-methylphenyl)-1,1'-biphenyl-4,4'-diamine, 2,2'-dimethyl-N'-(4"-diethoxymethyl silyl phenyl)-N,N,N'-tri(4"'-methylphenyl)-1,1'-biphenyl-4,4'-diamine, 2,2'-dimethyl-N'-(4"-dimethylethoxy silyl phenyl)-N,N,N'-tri(4"'-methylphenyl)-1,1'-biphenyl-4,4'-diamine, 2,2'-dimethyl-N,N,N'-tri(4"'-methylphenyl)-N'-(4"-trimethoxy silyl phenyl)-1,1'-biphenyl-4,4'-diamine, 2,2'-dimethyl-N'-(4"-dimethoxymethyl silyl phenyl)-N,N,N'-tri(4"'-methylphenyl)-1,1'-biphenyl-4,4'-diamine, 2,2'-dimethyl-N'-(4"-dimethylmethoxy silyl phenyl)-N,N,N'-tri(4"'-methylphenyl)-1,1'-biphenyl-4,4'-diamine, N'-(4"-triethoxy silyl phenyl)-N,N,N'-trenphenyl-1,1'-biphenyl-3,3'-diamine, N'-(4"-diethoxymethyl-silyl phenyl)-N,N,N'-triphenyl-1,1'-biphenyl-3,3'-diamine, N'-(4"-dimethylethoxy silyl phenyl)-N,N,N'-triphenyl 1,1'-biphenyl-3,3'-diamine, N'-(4"-trimethoxy silyl phenyl)-N,N,N'-triphenyl-1,1'-biphenyl-3,3'-diamine, N'-(4"-dimethoxymethyl silyl phenyl)-N,N,N'-triphenyl 1,1'-biphenyl-3,3'-diamine, N'-(4"-dimethylmethoxy silyl phenyl)-N,N,N'-triphenyl-1,1'-biphenyl-3,3'-diamine, N'-(4"-triethoxy silyl phenyl)-N,N,N'-tri(4"'-methylphenyl)-1,1'-biphenyl-3,3'-diamine, N'-(4"-diethoxymethyl silyl phenyl)-N,N,N'-tri(4"'-methylphenyl)-1,1'-biphenyl-3,3'-diamine, N'-(4"-dimethylethoxy silyl phenyl)-N,N,N'-tri(4"'-methylphenyl)-1,1'-biphenyl-3,3'-diamine, N,N,N'-tri(4"'-methylphenyl)-N'-(4"-trimethoxy silyl phenyl)-1,1'-biphenyl-3,3'-diamine, N'-(4"-dimethoxymethyl silyl phenyl)-N,N,N'-tri(4"'-methylphenyl)-1,1'-biphenyl-3,3'-diamine, N'-(4"-dimethylmethoxy silyl phenyl)-N,N,N'-tri(4"'-methylphenyl)-1,1'-biphenyl-3,3'-diamine, 1-(triethoxysilyl)-pyrene, 1-(diethoxymethyl silyl)-pyrene, 1-(dimethylethoxy silyl)-pyrene, 1-(trimethoxy silyl)-pyrene, 1-(dimethoxymethyl silyl)-pyrene, 1-(dimethylmethoxy silyl)-pyrene, 2-(triethoxysilyl)-pyrene, 2-(diethoxymethyl silyl)-pyrene, 2-(dimethylethoxy silyl)-pyrene, 2-(trimethoxy silyl)-pyrene, 2-(dimethoxymethyl silyl)-pyrene, 2-(dimethylmethoxy silyl)-pyrene, 4-(triethoxysilyl)-pyrene, 4-(diethoxymethyl silyl)-pyrene, 4-(dimethylethoxy silyl)-pyrene, 4-(trimethoxy silyl)-pyrene, 4-(dimethoxymethyl silyl)-pyrene, 4-(dimethylmethoxy silyl)-pyrene, 1-(triethoxysilyl)-naphthacene, 1-(diethoxymethyl silyl)-naphthacene, 1-(dimethylethoxy silyl)-naphthacene, 1-(trimethoxy silyl)-naphthacene, 1-(dimethoxymethyl silyl)-naphthacene, 1-(dimethylmethoxy silyl)-naphthacene, 2-(triethoxysilyl)-naphthacene, 2-(diethoxymethyl silyl)-naphthacene, 2-(dimethylethoxy silyl)-naphthacene, 2-(trimethoxy silyl)-naphthacene, 2-(dimethoxymethyl silyl)-naphthacene, 2-(dimethylmethoxy silyl)-naphthacene, 5-(triethoxysilyl)-naphthacene, 5-(diethoxymethyl silyl)-naphthacene, 5-(dimethylethoxy silyl)-naphthacene, 5-(trimethoxy silyl)-naphthacene, 5-(dimethoxymethyl silyl)-naphthacene, 5-(dimethylmethoxy silyl)-naphthacene, 1-(triethoxysilyl)-triphenylene 1-(diethoxymethyl silyl)-triphenylene, 1-(dimethylethoxy silyl)-triphenylene, 1-(trimethoxy silyl)-triphenylene, 1-(dimethoxymethyl silyl)-triphenylene, 1-(dimethylmethoxy silyl)-triphenylene, 2-(triethoxysilyl)-triphenylene, 2-(diethoxymethyl silyl)-triphenylene, 2-(dimethylethoxy silyl)-triphenylene, 2-(trimethoxy silyl)-triphenylene, 2-(dimethoxymethyl silyl)-triphenylene, 2-(dimethylmethoxy silyl)-triphenylene, 1-(triethoxysilyl)-perylene, 1-(diethoxymethyl silyl)-perylene, 1-(dimethylethoxy silyl)-perylene, 1-(trimethoxy silyl)-perylene, 1-(dimethoxymethyl silyl)-perylene, 1-(dimethylmethoxy silyl)-perylene, 2-(triethoxysilyl)-perylene, 2-(diethoxymethyl silyl)-perylene, 2-(dimethylethoxy silyl)-perylene, 2-(trimethoxy silyl)-perylene, 2-(dimethoxymethyl silyl)-perylene, 2-(dimethylmethoxy silyl)-perylene, 3-(triethoxysilyl)-perylene, 3-(diethoxymethyl silyl)-perylene, 3-(dimethylethoxy silyl)-perylene, 3-(trimethoxy silyl)-perylene, 3-(dimethoxymethyl silyl)-perylene, 3-(dimethylmethoxy silyl)-perylene.

The silicon-containing compound of the present invention and silicon-containing compound used as a surface-treating agent of the electrode of the present invention can be synthesized by various methods. For example, when the silicon-containing compound has an aromatic amine group on the silicon atom, the compound can be synthesized by the method shown in the following reaction scheme.

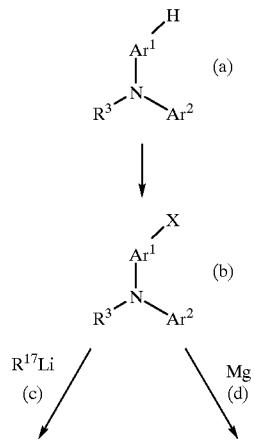

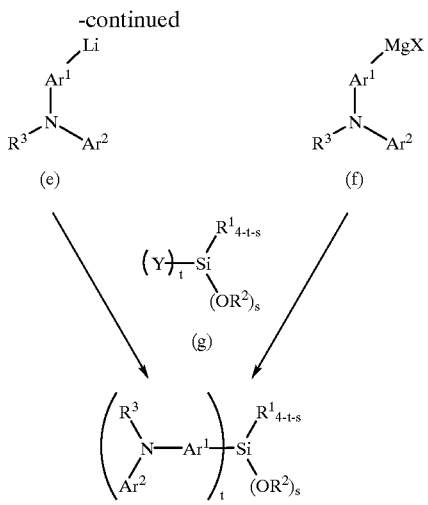

wherein $R^1$ to $R^3$, $Ar^1$, $Ar^2$, t and s are as defined above; $R^{17}$ represents an alkyl group; X represents a halogen atom; and Y represents a halogen atom or an alkoxy group.

That is, as shown in the reaction scheme, a halogenated amine compound represented by the formula [b] can be obtained by reacting an amine compound represented by the formula [a], produced by a known method, at a temperature within the range preferably from −20 to 150° C., more preferably from 0 to 100° C., most preferably from 10 to 60° C., for preferably 30 minutes to 24 hours, more preferably from 2 to 18 hours, most preferably from 4 to 10 hours to directly halogenate $Ar^1$, using a halogenating agent such as N-bromosuccinimide, bromine, pyridinium hydrobromide perbromide, etc. The halogen atom is not specifically limited, and may be fluorine atom, chlorine atom, bromine atom or iodine atom. Examples of a solvent for synthesis of the halogenated amine compound represented by the formula [b] include carbon tetrachloride, N,N-dimethylformamide, acetic acid and the like.

Then, carbon atoms to which the halogen atom is linked are subjected to lithiation or Grignard reaction by reacting the halogenated amine compound [b] with an organolithium reagent [c] or metal magnesium [d] to obtain a lithium compound represented by the formula [e] or a Grignard compound represented by the formula [f].

As the method, a known method can be used. For example, in case of the lithiation, the above halogenated amine compound [b] is dissolved in an ether solvent and then an equimolar amount of an organolithium reagent is added dropwise to the solution. A dropping temperature is from preferably −80 to 0° C., more preferably from −80 to −20° C., most preferably from −80 to −40° C. A reaction time is preferably from 10 minutes to 10 hours, more preferably from 30 minutes to 6 hours, most preferably from 1 to 3 hours.

Examples of the ether solvent to be used include diethyl ether, ethylene glycol dimethyl ether, ethylene glycol diethyl ether, diethylene glycol dimethyl ether, diethylene glycol diethyl ether, tetrahydrofuran, dioxane, diisopropyl ether, di-n-butyl ether and the like.

Examples of the organolithium reagent to be used include n-butyllithium, sec-butyllithium, tert-butyllithium, methyllithium, lithium diisopropylamide and the like. These organolithium reagents are used after diluting with an organic solvent.

Also in case of the Grignard reaction, the same solvent as that used in case of the lithiation can be used. Firstly, an equimolar to two-fold molar amount of a metal magnesium and a solvent are charged in a reaction vessel and a solution prepared by diluting the above halogenated amine compound [b] with a solvent is added dropwise. Then, the Grignard reaction is performed by stirring at a temperature within the range preferably from 0 to 150° C., more preferably from 25 to 100° C., most preferably from 50 to 80° C. for preferably 1 to 24 hours, more preferably from 3 to 18 hours, most preferably from 5 to 10 hours.

Furthermore, the compound represented by the general formula (1) of the present invention can be obtained by reacting the above lithium compound [e] or a Grignard compound [f] with an alkoxysilane compound represented by the formula [g] by using a known method. A reaction temperature is preferably from −80 to 0° C., more preferably from −80 to −20° C., most preferably from −80 to −40° C. A reaction time is preferably from 10 minutes to 10 hours, more preferably from 30 minutes to 6 hours, most preferably from 1 to 3 hours.

The silicon-containing compound having a condensed polycyclic aromatic group on the silicon atom, which is used as a surface-treating agent of the electrode of the present invention, can also be produced by the method shown in the following reaction scheme.

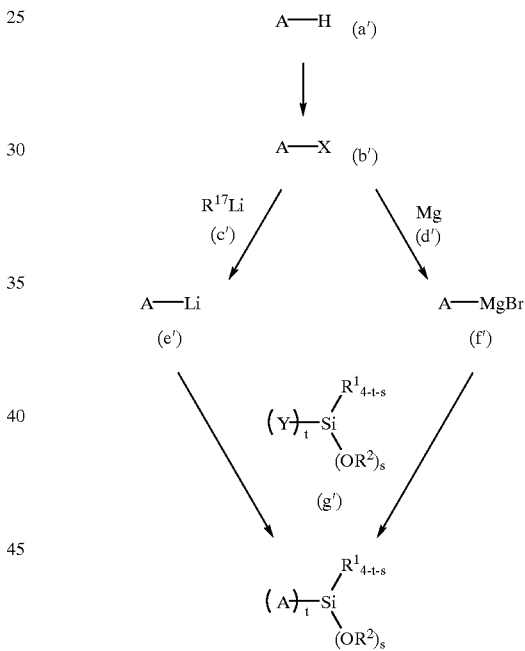

wherein $R^1$, $R^2$, A, t and s are as defined above; $R^{17}$ represents an alkyl group; X represents a halogen atom; and Y represents a halogen atom or an alkoxy group.

That is, as shown in the reaction scheme, a halogenated condensed polycyclic aromatic compound represented by the formula (b') can be obtained by reacting a condensed polycyclic aromatic compound represented by the formula (a'), produced by a known method, at a temperature within the range preferably from −20 to 150° C., more preferably from 0 to 100° C., most preferably from 10 to 60° C., for preferably 30 minutes to 24 hours, more preferably from 2 to 18 hours, most preferably from 4 to 10 hours to directly halogenate a condensed polycyclic aromatic group A, using a halogenating agent such as N-bromosuccinimide, bromine, pyridinium hydrobromide perbromide, etc. The halogen atom is not specifically limited, and may be fluorine atom, chlorine atom, bromine atom or iodine atom. Examples of a solvent for synthesis of the halogenated condensed polycyclic aromatic compound represented by the formula (b') include carbon tetrachloride, N,N-dimethylformamide, acetic acid and the like.

Then, carbon atoms to which the halogen atom is linked are subjected to lithiation or Grignard reaction by reacting the halogenated condensed polycyclic aromatic compound (b') with an organolithium reagent (c') or metal magnesium (d') to obtain a lithium compound represented by the formula (e') or a Grignard compound represented by the formula (f').

As the method, a known method can be used. For example, in case of the lithiation, the above halogenated condensed polycyclic aromatic compound (b') is dissolved in an ether solvent and then an equimolar amount of an organolithium reagent is added dropwise to the solution. A dropping temperature is preferably from −80 to 0° C., more preferably from −80 to −20° C., most preferably from −80 to −40° C. A reaction time is from preferably 10 minutes to 10 hours, preferably from more 30 minutes to 6 hours, most preferably from 1 to 3 hours.

Examples of the ether solvent to be used include diethyl ether, ethylene glycol dimethyl ether, ethylene glycol diethyl ether, diethylene glycol dimethyl ether, diethylene glycol diethyl ether, tetrahydrofuran, dioxane, diisopropyl ether, di-n-butyl ether and the like.

Examples of the organolithium reagent to be used include n-butyllithium, sec-butyllithium, tert-butyllithium, methyllithium, lithium diisopropylamide and the like. These organolithium reagents are used after diluting with an organic solvent.

Also in case of the Grignard reaction, the same solvent as that used in case of the lithiation can be used. Firstly, an equimolar to two-fold molar amount of metal magnesium and a solvent are charged in a reaction vessel and a solution prepared by diluting the above halogenated condensed polycyclic aromatic compound (b') with a solvent is added dropwise. Then, the Grignard reaction is performed by stirring at a temperature within the range preferably from 0 to 150° C., more preferably from 25 to 100° C., most preferably from 50 to 80° C. for preferably 1 to 24 hours, more preferably from 3 to 18 hours, most preferably from 5 to 10 hours.

Furthermore, the compound represented by the general formula (3) of the present invention can be obtained by reacting the above lithium compound (e') or a Grignard compound (f') with an alkoxysilane compound represented by the formula (g') by using a known method. A reaction temperature is preferably from −80 to 0° C., more preferably from −80 to −20° C., most preferably from −80 to −40° C. A reaction time is from preferably 10 minutes to 10 hours, more preferably from 30 minutes to 6 hours, most preferably from 1 to 3 hours.

A solvent used in the reaction of the alkoxysilane compound may be any one capable of dissolving a raw material and a reaction product, and is not specifically limited. For example, there can be used aromatic hydrocarbons such as toluene, xylene, benzene, etc.; aliphatic hydrocarbons such as dodecane, heptane, hexane, cyclohexane, etc.; and ether solvents such as diethyl ether, tetrahydrofuran, tetrahydropyran, diethylene glycol dimethyl ether, dioxane, etc.

In the present invention, since the alkoxysilane compound used in the production of the silicon-containing compound is apt to be easily hydrolyzed in case of using in the reaction, the reaction may be preferably performed under an inert atmosphere containing no water, such as dry nitrogen, argon, etc. so that no water is introduced. Furthermore, water in the solvent for the above reaction is preferably removed. When the water content is large, alkoxy groups of the raw material and product are hydrolyzed and polycondensated, which results in decrease of the yield of the desired product.

The reaction product obtained by the above reaction is preferably used after purifying by a known method such as recrystallization, distillation, column chromatography and the like.

In the present invention, a method of treating the surface of an electrode (e.g. transparent conductive electrode, etc.) with a silicon-containing compound can be performed by diluting the silicon-containing compound with a suitable solvent to prepare a treating-solution and bringing the treating-solution into contact with the electrode.

The solvent used for dilution may be any one capable of dissolving the silicon-containing compound, and is not specifically limited. For example, there can be used aromatic hydrocarbons such as toluene, xylene, benzene, etc.; aliphatic hydrocarbons such as dodecane, heptane, hexane, cyclohexane, etc.; and ether solvents such as diethyl ether, tetrahydrofuran, tetrahydropyran, diethylene glycol dimethyl ether, dioxane, etc.

In the present invention, the concentration of the silicon-containing compound in the treating-solution is not specifically limited as far as the silicon-containing compound is dissolved, but is preferably from 0.1 to 20% by weight, more preferably from 0.5 to 10% by weight. It is also possible to add a catalyst to this treating-solution, if necessary. Examples of the catalyst include ammonia, trimethylamine, triethylamine and a N-alkyl-substituted compound of piperazine or piperidine. An amount of the catalyst added is preferably from 0.1 to 10% by weight.

A method of treating the electrode by contacting with the treating-solution is not specifically limited, but a method of immersing the electrode in the treating-solution in an inert atmosphere containing no water (e.g. dry nitrogen, argon, etc.) is preferable.

Furthermore, the electrode after treatment is preferably used after the compound remaining reacted with the electrode is removed by washing with a solvent capable of dissolving the silicon-containing compound and/or a solvent which is inert to the silicon-containing compound (e.g. acetone, etc.).

In the present invention, as the electrode to be treated with the silicon-containing compound, various materials having conductivity can be used. Examples of the material include 1̇ metal, 2̇ glass or plastic on which a metal thin film is formed, 3̇ conductive polymer and the like. Specific examples of the metal include aluminum, copper, tin, platinum, gold, silver, vanadium, molybdenum, chromium, cadmium, titanium, nickel, indium, stainless steel, brass and the like. Examples of the metal thin film to be formed on the surface of glass or plastic include thin films of the above metals. Examples of the conductive polymer include polyaniline, polyacetylene and the like.

In the present invention, when a transparent or semitransparent electrode is used as the electrode to be treated with the silicon-containing compound, conductive metal oxide films and semitransparent thin films of the above mentioned metals are used. Specifically, films composed of indium oxide-tin (ITO), tin oxide, zinc oxide, etc. and semitransparent thin films of aluminum, copper, tin, platinum, gold, silver, vanadium, molybdenum, chromium, cadmium, titanium, nickel, indium, stainless steel, brass, etc. are used. In the present invention, an electrode on which an oxide is formed is preferable. Specific examples thereof include film made by using the above metal oxide and thin metal films wherein an oxide film is naturally formed on the metal surface, etc.

Examples of the method of producing a thin film include vacuum deposition method, sputtering method, plating method and the like.

In the present invention, the surface of the electrode to be treated with the silicon-containing compound is preferably cleaned by using treating methods such as acid or alkaline washing, detergent washing, solvent washing, plasma washing, ozone treatment, ultraviolet irradiation, ultraviolet irradiation under an ozone atmosphere, etc. alone or in combination thereof before performing the surface treatment.

The organic EL device of the present invention will be described hereinafter.

The structure of the organic EL device of the present invention may be any organic EL device having at least one organic layer between a pair of electrodes of an anode and a cathode, at least one of which is transparent or semitransparent, wherein the anode is treated with the surface-treating agent of the present invention, and is not specifically limited. Therefore, any known structure can be employed. Alternatively, various modifications can be made without departing from the scope of the present invention.

Specific examples of the structure of the organic EL device of the present invention include ① device structure having a pair of electrodes on both sides of a light emitting layer, ② device structure made by laminating a light emitting layer and a hole transporting layer and providing an cathode on the surface of the light emitting layer and an anode on the surface of the hole transporting layer, ③ device structure made by laminating a light emitting layer and an electron transporting layer and providing an anode on the surface of the light emitting layer and a cathode on the surface of the electron transporting layer, ④ device structure made by laminating a hole transporting layer, a light emitting layer and an electron transporting layer in this order and providing an anode on the surface of the hole transporting layer and a cathode on the surface of the electron transporting layer.

In all of device structures, the light emitting layer contains a light emitting material, or a light emitting material and a charge transporting material (hole transporting material and/or electron transporting material), the hole transporting layer contains a hole transporting material, and the electron transporting layer contains an electron transporting material.

The shape, size, material and fabrication method of the organic EL devices having these structures of the present invention are appropriately selected according to applications of the organic EL device, and are not specifically limited.

With respect to the light emitting layer, hole transporting layer and electron transporting layer, the case where a single layer is used and the case where a plurality of layers are used in combination are also included in the present invention.

The hole transporting material used in the organic EL device of the present invention is not specifically limited, and known materials can be used. Examples of the hole transporting material include low molecular weight compounds such as pyrazoline derivative, arylamine derivative, stilbene derivative, etc.; and polymeric compounds such as poly (N-vinylcarbazole), polysilane, etc. Specifically, N,N'-di(3"-methylphenyl)-N,N'-diphenyl-1,1'-biphenyl-4,4'-diamine is preferable as the low molecular weight compound, and poly (N-vinylcarbazole) and polysilane compound are preferable as the polymeric compound.

When the hole transporting material and the light emitting material are used in a mixture, an amount of the hole transporting material and light emitting material used varies depending on the kind of the compound to be used. Therefore, the amount is appropriately decided as far as sufficient film forming property and light emitting characteristics are not inhibited. The amount of the hole transporting material is normally from 1 to 40% by weight, preferably from 2 to 30% by weight, based on the light emitting material.

The polysilane compound, which can be used as the hole transporting layer or the hole transporting material of a layer containing the hole transporting material and light emitting material, may contain one or more repeating units represented by the following general formula (4):

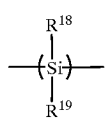

(4)

wherein $R^{18}$ and $R^{19}$ independently represent an alkyl group having 1 to 10 carbon atoms, a cycloalkyl group having 10 carbon atoms or less, an aryl group having 6 to 24 carbon atoms or an aralkyl group having 7 to 26 carbon atoms, and/or a repeating unit represented by the following general formula (5):

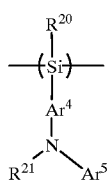

(5)

wherein $R^{20}$ represents an alkyl group having 1 to 10 carbon atoms, a cycloalkyl group having 10 carbon atoms or less, an aryl group having 6 to 24 carbon atoms or an aralkyl group having 7 to 26 carbon atoms; $R^{21}$ represents an alkyl group having 1 to 10 carbon atoms, a cycloalkyl group having 10 carbon atoms or less, an aryl group having 6 to 24 carbon atoms or an aralkyl group having 7 to 26 carbon atoms; $Ar^4$ represents an arylene group having 6 to 24 carbon atoms; $Ar^5$ represents an aryl group having 6 to 24 carbon atoms; and a ring may be formed between $Ar^4$ and $Ar^5$, $Ar^4$ and $R^{21}$, or $R^{21}$ and $Ar^5$.

$R^{18}$, $R^{19}$, $R^{20}$ or $R^{21}$ in the repeating units represented by the general formulas (4) and (5) independently represent a straight-chain or branched alkyl group having 1 to 10 carbon atoms, a cycloalkyl group having 10 carbon atoms or less, an aryl group having 6 to 24 carbon atoms or an aralkyl group having 7 to 26 carbon atoms. $R^{21}$ is preferably an aryl group having 6 to 24 carbon atoms, particularly a phenyl group.

In $R^{18}$, $R^{19}$, $R^{20}$ and $R^{21}$, the aryl(e.g.the phenyl group)- and aralkyl groups may be substituted with a straight-chain or branched alkyl group having 1 to 6 carbon atoms and a cycloalkyl group having 6 carbon atoms or less. Specific examples of the substituent of the aryl and aralkyl groups include methyl group, ethyl group, n-propyl group, isopropyl group, n-butyl group, sec-butyl group, tert-butyl group, pentyl group, hexyl group, cyclohexyl group, etc., preferably methyl group and ethyl group.

Specific examples of $R^{18}$, $R^{19}$, $R^{20}$ or $R^{21}$ independently include alkyl groups such as methyl group, ethyl group, n-propyl group, isopropyl group, n-butyl group, sec-butyl group, tert-butyl group, pentyl group, hexyl group, octyl group, dodecyl group, etc.; cycloalkyl groups such as cyclohexyl group, etc.; aryl groups such as phenyl group, naphthyl group, anthryl group, biphenyl group, etc.; and aralkyl groups such as benzyl group, phenethyl group, p-methylbenzyl group, etc.

$Ar^4$ in the repeating unit represented by the general formula (5) is preferably an arylene group having 6 to 24 carbon atoms. Specific examples thereof a phenylene group, a naphthylene group, an anthrylene group, a biphenylene group, etc., preferably a phenylene group.

$Ar^5$ in the repeating unit represented by the general formula (5) is preferably an aryl group having 6 to 24 carbon atoms. Specific examples thereof a phenyl group, a naphthyl group, an anthryl group, a biphenyl group, etc., preferably a phenyl group.

The arylene group for $Ar^4$ and the aryl group for $Ar^5$ may be substituted with a straight-chain or branched alkyl group having 1 to 6 carbon atoms and a cycloalkyl group having 6 carbon atoms or less. Specific examples of the substituent of the arylene and aryl groups include methyl group, ethyl group, n-propyl group, isopropyl group, n-butyl group, sec-butyl group, tert-butyl group, pentyl group, hexyl group, cyclohexyl group, etc., preferably methyl group and ethyl group.

In the present invention, Ip1 preferably satisfies the following numeral formula (I):

$$W \leq Ip1 \leq Ip2 \tag{I}$$

wherein Ip1 is an ionization potential of a silicon-containing compound; W is a work function of an anode to be treated with the silicon-containing compound; and Ip2 is an ionization potential of an organic layer to be formed on the anode to be treated with the silicon-containing compound.

Ip1 more preferably satisfies the following numeral formula (II):

$$Ip1 \approx (W+Ip2)/2 \tag{II}$$

In the present invention, holes to be injected from an anode such as transparent conductive electrode into an organic layer adjacent to the anode pass through a two-stage process of injection to a hole transporting arylamine derivative structure and/or a condensed polycyclic aromatic ring contained in the silicon-containing compound of the present invention and further injection to the organic layer. In each injection process, holes must be injected over an potential barrier of Ip1-W and Ip2-Ip1. If Ip1 satisfies the above formula, each potential barrier of the hole injection process becomes smaller than an potential barrier Ip2-W between the anode and the organic layer. Therefore, holes easily are injected and the injection efficiency of holes to be injected from the anode to the organic layer is improved.

In the present invention, when the ionization potential Ip1 of the silicon-containing compound satisfies the expression W>Ip1 or Ip1>Ip2, the potential of any hole injection process is larger than the potential barrier Ip2-W between the anode and the organic layer and holes do not be injected easily. Therefore, the injection efficiency of holes to be injected from the anode to the organic layer is sometimes lowered.

A method of producing a polysilane compound used as the hole transporting material of the organic electroluminescence device of the present invention is not specifically limited, but the same method as that described in Journal of Organometallic Chemistry, Vol. C27, page 198 (1980) or Journal of Polymer Science: Polymer Chemistry Edition, Vol. 22, page 159 (1984) can be used.

That is, a polysilane compound containing at least one repeating unit represented by the above general formula (4) and/or a repeating unit represented by the above general formula (5) on the main skeleton can be produced by bringing a dihalosilane monomer represented by the following general formula (6):

(6)

wherein $R^{18}$ and $R^{19}$ are as defined above; and X represents a halogen atom, or a dihalosilane monomer represented by the following general formula (7):

(7)

wherein $R^{20}$, $R^{21}$, $Ar^4$ and $Ar^5$ are as defined above; and X represents a halogen atom, or a mixture of two or more kinds of dihalosilane monomers having different side chain, represented by the above general formula (6) and/or a dihalosilane monomer represented by the above general formula (7), into contact with a condensed catalyst of an alkaline metal to perform dehalogenation and polycondensation under a high-purity inert atmosphere wherein oxygen and water are removed.

The light emitting material of the light emitting layer used in the organic EL device of the present invention, or the light emitting material of the layer containing the hole transporting material and light emitting material is not specifically limited, and various materials can be applied. A light emitting low molecular weight compound and a light emitting polymer are preferable, and the light emitting polymer is more preferable.

The light emitting low molecular weight compound is not specifically limited, and there can be used naphthalene and a derivative thereof; anthracene and a derivative thereof; perylene and a derivative thereof; a polymethine, coumarine and cyanine pigments; 8-hydroxyquinoline and a metal complex of a derivative thereof; a aromatic amine; and tetraphenylcyclopentane and a derivative thereof. Specifically, there can be known light emitting low molecular weight compounds described in Japanese Patent Kokai Publication Nos. 57-51781 and 59-194393.

The light emitting polymer, which can be used as the light emitting material, is not specifically limited, and examples thereof include polyphenylenevinylene, polyarylene, polyalkylthiophene, polyalkylfluorene and the like. Particularly, the following polyphenylenevinylene derivative is preferable.

The light emitting polymer used preferably in the light emitting layer of theorganic EL device of the present invention will be explained hereinafter.

The light emitting polymer is a polymer containing a repeating unit represented by the following general formula (8): in an amount of 50% by mol based on the whole repeating unit

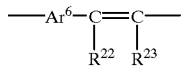

(8)

wherein $Ar^6$ represents an arylene group or a heterocyclic compound group having 4 to 20 carbon atoms which take part in a conjugated bond; $R^{22}$ and $R^{23}$ independently represent a group selected from the group consisting of hydrogen, an alkyl group having 1 to 20 carbon atoms, an aryl group having 6 to 20 carbon atoms, a heterocyclic compound group having 4 to 20 carbon atoms and cyano group. The repeating unit represented by the general formula (8) is preferably not less than 70% based on the whole repeating unit, although it depends on the structure of the repeating unit. The light emitting polymer may contain a divalent aromatic compound group or a derivative thereof, a divalent heterocyclic compound group or a derivative thereof, and a group obtained by combining them, as a repeating unit other than the repeating unit represented by the general formula (8). Furthermore, the repeating unit represented by the general formula (8) and other repeating unit may be linked in a non-conjugated unit having an ether group, an ester group, an amide group, an imide group, etc., or the non-conjugated portion may be contained in the repeating unit.

In the light emitting polymer used in the organic EL device of the present invention, $Ar^6$ of the general formula (8) is an arylene group or a heterocyclic compound group having 4 to 20 carbon atoms which take part in a conjugated bond, and examples thereof include a divalent aromatic compound group or a group of a derivative thereof, divalent heterocyclic compound group or a group of a derivative thereof, which are described below, and a group obtained by combining them.

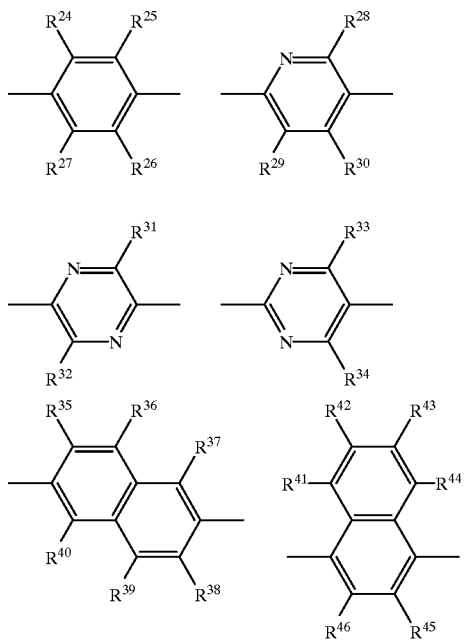

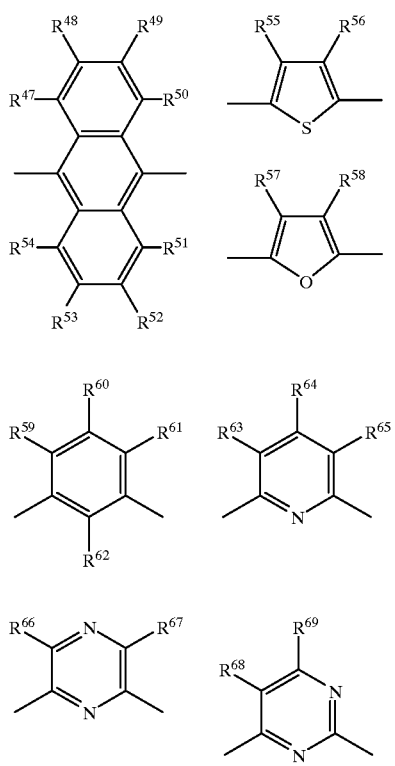

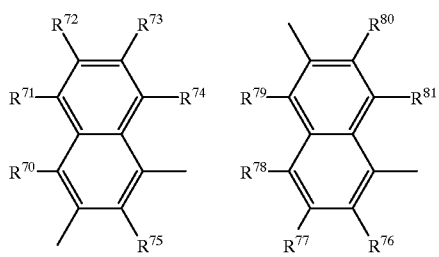

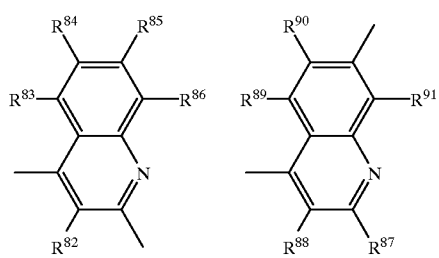

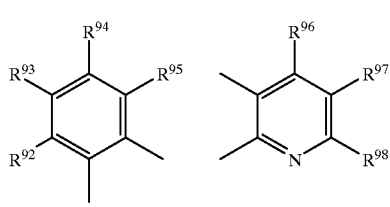

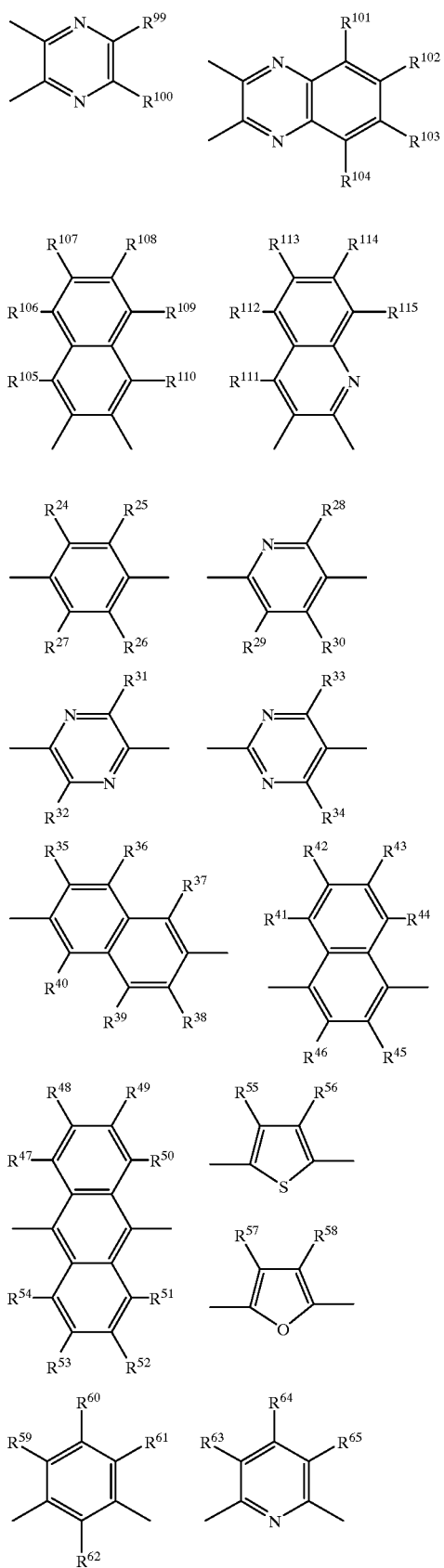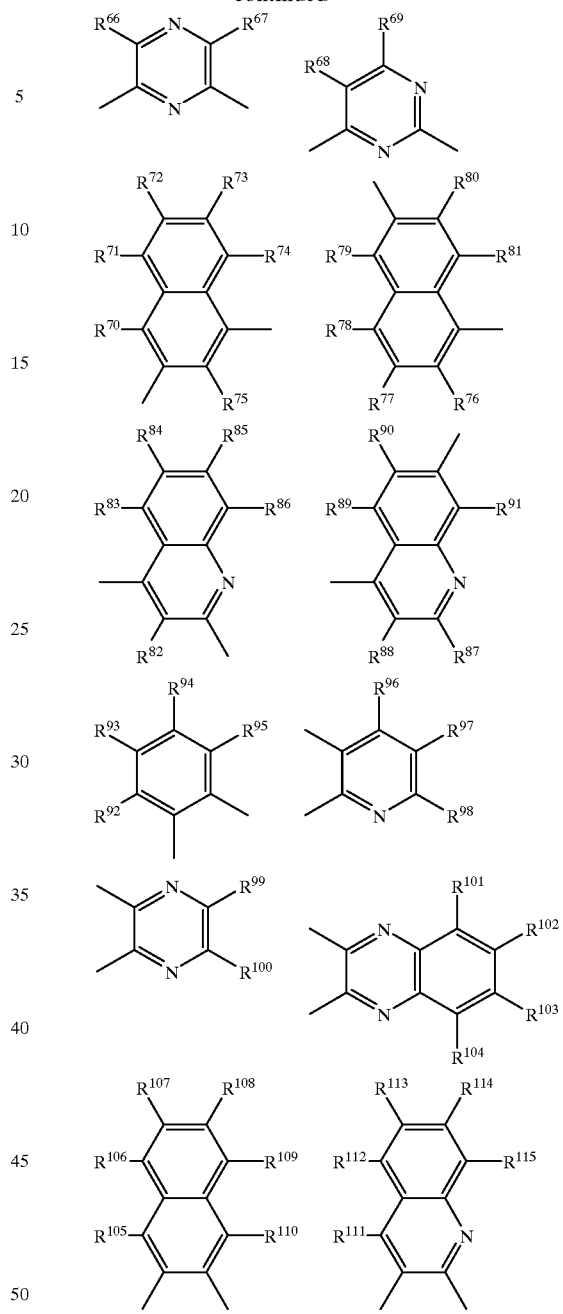

wherein $R^{24}$ to $R^{115}$ independently represent a group selected from the group consisting of hydrogen, alkyl, alkoxy and alkylthio groups having 1 to 20 carbon atoms, aryl and aryloxy groups having 6 to 18 carbon atom and heterocyclic compound group having 4 to 14 carbon atoms.

Among them, phenylene group, substitited-phenylene group, biphenylene group, substituted-biphenylene group, naphthalenediyl group, substituted-naphthalenediyl group, anthracene-9,10-diyl group, substituted-anthracene-9,10-diyl group, pyridine-2,5-diyl group, thienylene group or substituted-thienylene group is preferable. More preferable groups are phenylene group, biphenylene group, naphthalenediyl group, pyridine-2,5-diyl and thienylene group.

When $R^{22}$ and $R^{23}$ of the general formula (8) is a substituent other than the hydrogen or cyano group, examples of the alkyl group include methyl group, ethyl group, n-propyl group, isopropyl group, n-butyl group, sec-butyl group, tert-butyl group, pentyl group, hexyl group, octyl group, dodecyl group, lauryl group, etc., preferably methyl group, ethyl group, pentyl group, hexyl group, heptyl group and octyl group. Examples of the aryl group include phenyl group, 4-$C_1$–$C_{12}$ alkoxyphenyl group ($C_1$–$C_{12}$ shows 1 to 12 carbon atoms, the same rule applies correspondingly to the following), 4-$C_1$–$C_{12}$alkylphenyl group, 1-naphthyl group, 2-naphthyl group and the like.

In view of the solubility in organic solvents, $Ar^6$ of the general formula (8) has preferably one or more groups selected from the group consisting of alkyl, alkoxy or alkylthio group having 4 to 20 carbon atoms, aryl or aryloxy group having 6 to 18 carbon atoms, and heterocyclic compound group having 4 to 14 carbon atoms.

Examples of these groups are as follows. Examples of the alkyl group having 4 to 20 carbon atoms include n-butyl group, sec-butyl group, tert-butyl group, pentyl group, hexyl group, octyl group, decyl group, lauryl group, etc., preferably pentyl group, hexyl group, heptyl group and octyl group.

Examples of the alkoxy group having 4 to 20 carbon atoms include butoxy group, pentyloxy group, hexyloxy group, heptyloxy group, octyloxy group, decyloxy group, lauryloxy group, etc., preferably pentyloxy group, hexyoxyl group, heptyloxy group and octyloxy group.

Examples of the alkylthio group include butylthio group, pentylthio group, hexylthio group, heptylthio group, octylthio group, decylthio group, laurylthio group, preferably pentylthio group, hexylthio group, heptylthio group, octylthio group and the like.

Examples of the aryl group include phenyl group, 4-$C_1$–$C_{12}$ alkoxyphenyl group ($C_1$–$C_{12}$ shows that the number of carbon atoms is any one of 1 to 12), 4-$C_1$–$C_{12}$alkylphenyl group, 1-naphthyl group, 2-naphthyl group and the like.

Examples of the aryloxy group include phenoxy group. Examples of the heterocyclic compound group include 2-thienyl group, 2-pyrrolyl group, 2-furyl group, 2-, 3- or 4-pyridyl group and the like.

The number of these substituents varies depending on the molecular weight of the light emitting polymer and construction of the repeating unit. In order to obtain a light emitting polymer having high solubility, the number of these substituents is preferably at least one per molecular weight of 600.

The light emitting polymer used in the organic EL device of the present invention may be a random, block or graft copolymer, or a polymer having an intermediate construction of them, e.g. a random copolymer having a block polymer tendency. In order to obtain a light emitting polymer having high quantum yield of fluorescence, the random copolymer having a block polymer tendency, or block or graft copolymer is preferable than a completely random copolymer.

Since the organic EL device of the present invention utilizes light emission from a thin film, a light emitting polymer having luminescence at the solid state is used.

Examples of the good solvent to the light emitting polymer include chloroform, methylene chloride, dichloroethane, tetrahydrofuran, toluene, xylene and the like. The light emitting polymer can be normally dissolved in these solvents in an amount of not less than 0.1% by weight, although it varies depending on the structure or molecular weight of the light emitting polymer.

The polystyrene-reduced molecular weight of the light emitting polymer used in the organic EL device of the present invention is preferably within the range from $10^3$ to $10^7$, and the degree of polymerization depends on the repeated structure and it's proportion. In view of the film forming property, the total number of the repeated structures is preferably within the range from 4 to 10000, more preferably from 5 to 3000, particularly from 10 to 200.

In the organic EL device of the present invention, when an electron transporting layer is further formed between the light emitting layer and cathode, an electron transporting material used in the electron transporting layer or used, together with the hole transporting material and light emitting material, has a function of transporting electron injected from the cathode to the light emitting layer. The electron transporting material is not specifically limited, and any electron transporting material can be used by selected from compounds which have hitherto been known.

Preferred examples of the electron transporting material include nitro-substituted fluorenone derivative, anthraquinodimethane derivative, diphenylquinone derivative, thiopyran dioxide derivative, heterocyclic tetracarboxylic anhydride, carbodiimide and the like.

Furthermore, preferred examples are fluorenylidene derivative, anthraquinodimethane derivative, anthrone derivative, oxadiazole derivative and the like. Although a metal complex of 8-hydroxyquinoline and a derivative thereof are disclosed as the material for forming the light emitting layer, they can also be used as the electron transporting material.

Next, a typical method of producing the organic EL device having a laminated structure. as one embodiment of the present invention will be described. As the pair of transparent or semitransparent electrodes composed of the anode and cathode, for example, those obtained by forming a transparent or semitransparent electrode on a transparent substrate such as transparent glass, transparent plastic, etc. can be used.

As the material of the anode, for example, there can be used conductive metal oxide films, semitransparent metal thin films and the like. Specifically, films made by indium-tin oxide (ITO), tin oxide, zinc oxide, Au, Pt, Ag, Cu, etc. are used. Examples of the production method include vacuum deposition method, sputtering method, plating method and the like.

These anodes are used after surface-treating with the above silicon-containing compound by using the above treating method.

In the present invention, a hole transporting layer containing a hole transporting material is formed on the anode treated with the silicon-containing compound. Examples of the method of forming the hole transporting layer include method of depositing the hole transporting material as a layer according to the vacuum deposition method, and method of forming a film by application of a coating solution prepared by dissolving the hole transporting material in a solvent or a coating solution prepared by dissolving a binder resin and the hole transporting material in a solvent. When the hole transporting material is a polymeric compound (e.g. polysilane compound, etc.), the method of forming a film by application is preferable.

The coating solution for forming the hole transporting layer by application can be prepared by dissolving the hole transporting material in the solvent, or dissolving the hole transporting material and binder resin in the solvent. The hole transporting layer can be formed by applying the coating solution, using a known method such as dipping method, spray coating method, wire bar coating method, doctor blade coating method, roll coating method, spin coating method and the like. It is preferable to dry with heating at a temperature within the range preferably from 30 to 300° C., more preferably from 60 to 200° C., under reduced pressure or an inert atmosphere after forming the hole transporting layer.

As the binder resin in which the hole transporting material is dispersed, various resins can be used and examples thereof include polycarbonate resin, polyarylate resin, polysulfone resin, polystyrene, polyacrylate resin, styrene-acrylic copolymer, ethylene-vinyl acetate copolymer, polypropylene resin, olefin polymer, polyvinyl chloride resin, vinyl chloride-vinyl acetate copolymer, polyester resin, alkyd resin, polyamide resin, polyurethane resin, epoxy resin, diallyl phthalate resin, silicone resin, ketone resin, polyvinyl butyral resin, polyether resin, phenol resin, phtotosetting resins (e.g. epoxyacrylate resin ,etc.) and the like. These binder resins can be used alone or in combination thereof.

The solvent, which is used for preparing the coating solution for forming the hole transporting layer, may be any one which dissolves the hole transporting material and binder resin, and various organic solvents can be used. Examples thereof include solvents such as alcohols (e.g. methanol, ethanol, isopropanol, etc.), aliphatic hydrocarbons (e.g. n-hexane, octane, cyclohexane, etc.), aromatic hydrocarbons (e.g. benzene, toluene, xylene, etc.), halogenated hydrocarbons (e.g. dichloromethane, dichloroethane, carbon tetrachloride, chlorobenzene, etc.), ethers (e.g. dimethyl ether, diethyl ether, tetrahydrofuran, ethylene glycol dimethyl ether, diethylene glycol dimethyl ether, etc.), ketones (e.g. acetone, methyl ethyl ketone, cyclohexanone, etc.), N,N'-dimethylformamide, dimethyl sulfoxide, etc. These solvents may be used alone or in combination thereof.

As the hole transporting layer, two or more known hole transporting materials may be used in combination. Alternatively, a second hole transporting layer may be formed adjacent to the hole transporting layer formed on the anode.

A film thickness of the hole transporting layer is preferably within the range from 1 nm to 1 $\mu$m, more preferably from 2 to 500 nm. In order to enhance the electroluminescence efficiency(luminance/current density) by increasing the current density, the film thickness is most preferably within the range from 5 to 100 nm.

Then, a light emitting layer containing an organic pigment having low molecular weight, a light emitting polymer, etc. as the light emitting material is formed. Examples of the method of forming the light emitting layer include a method of applying a melt, a solution or a mixed solution of these materials according to a spin coating method, a casting method, a dipping method, a bar coating method, roll coating method and the like. It is preferable to form a film by applying the solution or mixed solution according to a coating method such as spin coating method, casting method, dipping method, bar coating method, roll coating method and the like.

A film thickness of the light emitting layer is preferably within the range from 1 nm to 1 $\mu$m, more preferably from 2 to 500 nm. In order to enhance the electroluminescence efficiency by increasing the current density, the film thickness is preferably within the range from 5 to 100 nm.

When a thin film of the light emitting layer is formed by the application method, it is preferable to dry with heating at a temperature within the range preferably from 30 to 300° C., more preferably from 60 to 200° C., under reduced pressure or an inert atmosphere so as to remove the solvent after formation of the hole transporting layer and/or light emitting layer.

When an electron transporting layer is further laminated on the light emitting layer, it is preferable to form the electron transporting layer after the light emitting layer was formed by the above-described film forming method.

The method of forming the film of the electron transporting layer is not specifically limited, and there can be used vacuum deposition method in the powder state; application method such as spin coating method, casting method, dipping method, bar coating method, roll coating method, etc. after dissolving in the solution; or application method such as spin coating method, casting method, dipping method, bar coating method, roll coating method, etc. after mixing the polymeric compound with the electron transporting material in the solution or molten state, followed by dispersion.

The polymeric compound to be mixed is not specifically limited, but those which do not inhibit electron transport are preferable. Those whose absorption to visible light is not strong are preferably used.

Examples thereof include poly(N-vinylcarbazole) and a derivative thereof, polyaniline and a derivative thereof, polythiophene and a derivative thereof, poly(p-phenylenevinylene) and a derivative thereof, poly(2,5-thienylenevinylene) and a derivative thereof, polycarbonate, polyacrylate, polymethyl acrylate, polymethyl methacrylate, polystyrene, polyvinyl chloride, polysiloxane and the like. It is preferable to use the application method when using the polymeric compound because a film can be easily formed.

A film thickness of the electron transporting layer must be a thickness so that no pin hole is formed. When the film thickness is too large, the resistance of the device increase to require high driving voltage, unfavorably. Accordingly, the film thickness of the electron transporting layer is preferably within the range from 1 nm to 1 $\mu$m, more preferably from 2 to 500 nm, most preferably from 5 to 100 nm.

Then, an electrode is formed on the light emitting layer or electron transporting layer. This electrode serves as an electron injection cathode. The material is not specifically limited, but a material having small work function is preferable.

For example, there can be used Al, In, Mg, Ca, Li, Mg—Ag alloy, In—Ag alloy, Mg—In alloy, Mg—Al alloy, Mg—Li alloy, Al—Li alloy, graphite thin film and the like. As the method of producing the cathode, there can be used vacuum deposition method, sputtering method and the like.

In the organic EL device of the present invention, there is also used a method of forming an organic layer containing the hole transporting material and light. emitting or an organic material containing the hole transporting material, light emitting layer and electron transporting material on one electrode according to the same manner as that of forming the above hole transporting layer, and then forming the other electrode.

Since the organic EL device of the present invention is capable of forming the hole transporting layer and light emitting layer by the application method, an organic EL device having low driving voltage, high luminance and high electroluminescence efficiency can be easily fabricated through a simple production process.

The silicon-containing compound of the present invention is industrially useful as a surface-treating agent for improving mechanical and electric contact between an electrode and an organic layer of devices having an organic layer adjacent to the electrode (e.g. transparent conductive electrode, etc.) such as photoconductive device, organic electroluminescence device, spatial light modulator device, organic photoelectric conversion device and the like.

EXAMPLES

The following Examples further illustrate the present invention in detail but are not to be construed to limit the scope thereof.

In the following Examples, the polystyrene-reduced molecular weight of the polymer, e.g. polystyrene-reduced number-average molecular weight and weight-average molecular weight, was measured by gel permeation chromatography (Waters Co., Maxima-820,Column Ultrastyragel Linear) with tetrahydrofuran as an eluent. Structure analysis was performed by using $^1$H, $^{13}$C-NMR (Bruker Co., Model AC200P), mass spectrum (FD-MS) (mass analyzer manufactured by Nippon Denshi Co., Model JMS-SX102) and infrared absorption spectrum (IR) (manufactured by Nippon Biorad Co.).

The ionization potential was determined from the measured oxidation potential (Eox) by the following equation.

$$Ip (eV) = Eox + E(Ag/AgCl) + E(NHE)$$
$$= Eox + 0.196 + 4.5$$

where E(Ag/AgCl) is the potential of the Ag/AgCl electrode against the standard hydrogen electrode and E(NHE) is the potential of the standard hydrogen electrode against the vacuum level.

The oxidation potential was determined from a half-wave potential of voltamogram by cyclic voltammetry (POTENTIOSTAT/GALVANOSTAT 2000 and FUNCTION GENERATOR FG-02, manufactured by Toho Giken Co., Ltd: working electrode and counter electrode: platinum, reference electrode: Ag/AgCl electrode, sweep rate: 50 mV/second) of a dichloromethane solution (supporting electrolyte: 0.1 mol of tetra-n-butylammonium tetrafluoroborate) of a material to be measured (0.1 mmol).

Reference Synthesis Example 1

Synthesis of poly(methylphenylsilane)

In a 100 ml three neck flask dried at 200° C., 1.3 g of metal sodium was charged and 19 ml of dry toluene was added. An ultrasonic wave was applied to this flask with heating to 100–105° C. under a dry argon flow to disperse sodium in the form of a particle having an average particle diameter of not more than 50 μm. After heating to 62° C., 5.0 g of methylphenyldichlorosilane (LS-1490, manufactured by Shinetsu Kagaku Co., Ltd.) was added dropwise over about 20 minutes. Immediately after the completion of the dropwise addition, the flask was heated to 85° C. and the reaction was further performed for 40 minutes.

After the completion of the reaction, 20 ml of toluene and 3 ml of isopropyl alcohol were added to the above flask under an argon flow to deactivate the excess metal sodium. Furthermore, about 10 ml of distilled water was added to dissolve the violet precipitate. The residual precipitate was separated by a centrifugation operation and then washed twice with toluene to recover a soluble matter as a toluene solution. After the toluene solution was washed with water and dried over anhydrous magnesium sulfate, the solvent was distilled off to obtain a glassy substance. This glassy. substance was dissolved in tetrahydrofuran to form a tetrahydrofuran solution which was added to isopropyl alcohol to form a precipitate. This purification is repeated to obtain 0.8 g of a white solid. It was confirmed from the nuclear magnetic resonance absorption spectrum (NMR) that this white solid is poly(methylphenylsilane). The polystyrene-reduced weight-average molecular weight was $2.3 \times 10^5$ and the polystyrene-reduced number-average molecular weight was $6.2 \times 10^3$.

The oxidation potential of poly(methylphenylsilane) was measured by cyclic voltamogram. As a result, it was 0.93 V (reduced to oxidation potential on the basis of standard hydrogen electrode: 1.13 V, reduced to ionization potential: 5.63 eV).

Reference Synthesis Example 2

Synthesis of ethyl(4-(N,N-diphenylamino)phenyl) dichlorosilane

In a 100 ml two neck flask which was dried at 200° C., assembled while being hot, cooled under vacuum and filled with dry argon, 4.7 g of 4-(N,N-diphenylamino) bromobenzene was charged, molten and then dried under vacuum, and 20 ml of dry tetrahydrofuran distilled over sodium immediately before addition was added to dissolve 4-(N,N-diphenylamino)bromobenzene. Then, 9.4 ml of n-butyllithium (1.6 M hexane solution, manufactured by Aldrich Co.) was added dropwise at −78° C. and the mixture was reacted for 1 hour to produce 4-(N,N-diphenylamino) phenyllithium.

In a 100 ml two neck flask dried in the same manner, 3.4 g of ethyltrichlorosilane (LS-120, manufactured by Shinetsu Kagaku Co., Ltd.) distilled over calcium hydride immediately before addition and 15 ml of dry tetrahydrofuran were charged and, after cooling to −78° C., the above 4-(N,N-diphenylamino)phenyllithium was added dropwise. After the completion of the dropwise addition, the reaction was performed overnight and the excess ethyltrichlorosilane and solvent were distilled off, followed by distillation using a glass tube oven(Model CTO-350RG, manufactured by SIBATA SCIENTIFIC TECHNOLOGY LTD.) to obtain 2.8 g of (4-(N,N-diphenylamino)phenyl)dichlorosilane.

Synthesis of poly(ethyl(4-(N,N-diphenylamino) phenyl)silane)

A 50 ml three neck flask dried at 200° C. was equipped with a rubber septum and an argon seal, and then cooled with repeating evacuation and filling of dry argon. In this flask, 0.7 g of metal sodium was charged under a dry nitrogen atmosphere and 16 ml of toluene, which was dried over sodium and distilled immediately before addition, was added. This flask was set to an ultrasonic dispersion device (Model 450, manufactured by Branson Co.) under a dry argon flow and then an ultrasonic wave was applied with heating to 100–105° C. to disperse sodium in the form of a particle having an average particle diameter of 50 μm.

A 50 ml three neck flask dried in the same manner was equipped with a magnetic stirrer, a thermocouple and a rubber septum, and then 4.9 g of ethyl(4-(N,N-diphenylamino)phenyl)dichlorosilane synthesized above and 4 ml of dry toluene were added to form a solution. After this flask was heated to 80° C., the above sodium dispersion was added dropwise over about 10 minutes. The temperature in the flask was increased temporarily to 120° C. by the dropwise addition. The reaction has been performed for 4 hours since the beginning of the dropwise addition.

After the completion of the reaction, 20 ml of toluene and 3 ml of isopropyl alcohol were added to the above flask under an argon flow to deactivate the excess metal sodium. Furthermore, about 10 ml of distilled water was added to dissolve the violet precipitate. The precipitate was separated by a centrifugation operation and then washed twice with toluene to recover a soluble matter as a toluene solution. After the toluene solution was washed with water and dried over anhydrous magnesium sulfate, the solvent was distilled off to obtain a glassy substance. This glassy substance was dissolved in tetrahydrofuran to form a tetrahydrofuran solution which was added to isopropyl alcohol to form a precipitate. This purification is repeated to obtain 0.24 g of a white solid. It was confirmed from the nuclear magnetic resonance absorption spectrum (NMR) that this white solid is poly(ethyl(4-(N,N-diphenylamino)phenyl)silane). The polystyrene-reduced weight-average molecular weight was $2.3 \times 10^5$ and the polystyrene-reduced number-average molecular weight was $6.2 \times 10^3$.

The oxidation potential of poly(ethyl(4-(N,N-diphenylamino)phenyl)silane) was measured by cyclic voltamogram. As a result, it was 0.83 V (reduced to oxidation potential on the basis of standard hydrogen. electrode: 1.03 V, reduced to ionization potential: 5.53 eV).

Reference Synthesis Example 3
Synthesis of Light Emitting Polymer

A phosphonium salt was synthesized by reacting 2,5-dioctyloxy-p-xylylene dibromide with triphenylphosphine in an N,N-dimethylformamide solution. Then, 47.45 parts by weight of the resulting phosphonium salt and 6.7 parts by weight of terephthalaldehyde were dissolved in ethyl alcohol. An ethyl alcohol solution containing 5.8 parts by weight of lithium ethoxide was added dropwise to an ethyl alcohol solution of the phosphonium salt and dialdehyde, and the mixture was polymerized at room temperature for 3 hours. After standing overnight at room temperature, the precipitate was filtered off, washed with ethanol and then dissolved in chloroform. Ethanol was added to the solution to form a precipitate again. The precipitate was dried under reduced pressure to obtain 8.0 parts by weight of a polymer. This polymer is referred to as a light emitting polymer 1. The repeating unit and molar ratio of the light emitting polymer 1, which are calculated by the charging ratio of monomers, are shown below.

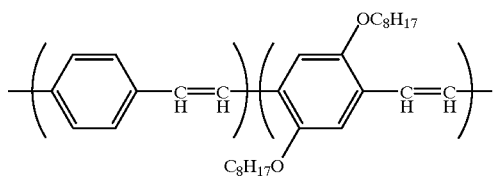

The molar ratio of two repeating units is 1:1 and two repeating units are alternatively bonded.

The polystyrene-reduced number-average molecular weight of the light emitting polymer 1 was $1.0 \times 10^4$. The structure of the light emitting polymer 1 was confirmed by the infrared absorption spectrum and NMR.

The oxidation potential of the light emitting polymer 1 was measured by cyclic voltamogram. As a result, it was 0.99 V (reduced to oxidation potential on the basis of standard hydrogen electrode: 1.19 V, reduced to ionization potential: 5.69 eV).

Example 1
Synthesis of Surface-treating Agent

A 300 ml two neck round bottom flask was filled with an argon gas to replace the atmosphere in the system by an inert atmosphere. In the flask, 20 g of N,N'-diphenyl-1,1'-biphenyl-4,4'-diamine, 50 g of 4-iodotoluene, 15 g or copper powder, 68 g of potassium hydroxide and 100 ml of dodecane were charged, and the mixture was continuously stirred at 180° C. for 35 hours. After the completion of the reaction, the reaction solution was cooled to room temperature and 100 ml of water was added. The product was extracted with 80 ml of toluene. The toluene solution of the extracted product was dried over anhydrous sodium sulfate and then filtered. After the solvent was distilled off under reduced pressure, the solution was concentrated to obtain a solid. The resulting solid was recrystallized from toluene/isopropyl alcohol solution to obtain 9.7 g of N,N'-di(4"-methylphenyl)-N,N'-diphenyl-1,1'-biphenyl-4,4'-diamine as a pale yellow crystal.

In a 500 ml two neck round bottom flask, 5 g of N,N'-di(4"-methylphenyl)-N,N'-diphenyl-1,1'-biphenyl-4,4'-diamine and 200 ml of N,N'-dimethylformamide were charged and the mixture was dissolved by heated to 40° C. A solution (100 ml) prepared by dissolving 0.86 g of N-bromosuccinimide in N,N'-dimethylformamide was slowly added dropwise at room temperature with vigorously stirring and, after the completion of the dropwise addition, the reaction was continuously performed for 1 hour. After the completion of the reaction, 1 ml of water was introduced in the reaction solution and the solvent was removed under reduced pressure. Then, 100 ml of water was added to deposit a product. The deposit was filtered, dried under reduced pressure and then purified by flash chromatography using toluene/hexane as an eluent to obtain 3.3 g of N'-(4'"-bromophenyl)-N,N'-di(4"-methylphenyl)-N-phenyl-1,1'-biphenyl-4,4'-diamine.

In a 100 ml two neck round bottom flask, 3.3 g of N'-(4'"-bromophenyl)-N,N'-di(4"-methylphenyl)-N-phenyl-1,1'-biphenyl-4,4'-diamine synthesized above and 30 ml of dry tetrahydrofuran were charged and the mixture was cooled to −78° C. 1.74 ml of a 1.6 M (mol/l) n-butyllithium/hexane solution was added dropwise and, after the completion of the dropwise addition, the reaction was continuously performed for 1 hour. The resulting reaction solution is referred to as a reaction solution A.

In another 100 ml two neck flask, 2.1 g of chlorotriethoxysilane and 10 ml of dry tetrahydrofuran were charged and the mixture was cooled to −78° C. To the mixture, the previously prepared reaction solution A was added. The reaction was continuously performed at −78° C. for 2 hours, followed by reaction at room temperature overnight. After the completion of the reaction, the solvent was distilled off and 40 ml of hexane was added to deposit a salt. The deposited salt was filtered and the filtrate was partially concentrated. The resulting hexane solution was cooled to deposit the desired product, thereby obtaining 1.5 g of a pale yellow viscous liquid.

It was confirmed from $^1$H-NMR and FD-MS spectrum that this liquid is N,N'-di(4"-methylphenyl)-N-phenyl-N'-(4'"-triethoxysilylphenyl)-1,1'-biphenyl-4,4'-diamine. Hereinafter, this is referred to as a surface-treating agent 1.

The oxidation potential of the resulting surface-treating agent 1 was measured by cyclic voltamogram. As a result, it was 0.77 V (reduced to oxidation potential on the basis of standard hydrogen electrode: 0.97 V, reduced to ionization potential: 5.47 eV).

Example 2
Synthesis of Surface-treating Agent

According to the same manner as that described in Example 1 except for using N,N,N',N'-tetraphenyl-1,1'-biphenyl-4,4'-diamine in place of N,N'-di(4"-methylphenyl)-N,N'-diphenyl-1,1'-biphenyl-4,4'-diamine synthesized from 4-iodotoluene and N,N'-diphenyl-1,1'-biphenyl-4,4'-diamine, N'-(4"-triethoxysilylphenyl)-N,N,N'-triphenyl-1,1'-biphenyl-4,4'-diamine was synthesized. Hereinafter, this is referred to as a surface-treating agent 2.

The oxidation potential of the resulting surface-treating agent 2 was measured by cyclic voltamogram. As a result, it was 0.83 V (reduced to oxidation potential on the basis of standard hydrogen electrode: 1.03 V, reduced to ionization potential: 5.53 eV).

Example 3
Synthesis of Surface-treating Agent

In a 2000 ml two neck round bottom flask, 250 g of triphenylamine and 1000 ml of N,N'-dimethylformamide were charged, and the mixture was dissolved by heating to 40° C. A solution (450 ml) prepared by dissolving 190 g of N-bromosuccinimide in N,N'-dimethylformamide was slowly added dropwise using a dropping funnel at room temperature with vigorously stirring and, after the completion of the dropwise addition, the reaction was continuously performed for 1 hour. After the completion of the reaction, 1 ml of water was introduced in the reaction solution and the solvent was removed under reduced pressure. Then, 500 ml of water was added to deposit a product. The deposit was filtered, dried under reduced pressure and then purified by distillation under reduced pressure to obtain 100 g of N-(4-bromophenyl)-N-phenyl-aminobenzene.

In a 300 ml two neck round bottom flask, 20 g of N-(4-bromophenyl)-N-phenyl-aminobenzene synthesized above and 100 ml of dry tetrahydrofuran were charged and the mixture was cooled to −78° C. 46.3 ml of a 1.6 M n-butyllithium/hexane solution was added dropwise and, after the completion of the dropwise addition, the reaction was continuously performed for 1 hour. The resulting reaction solution is refereed to as a reaction solution B.

In another 300 ml two neck flask, 18.4 g of chlorotriethoxysilane and 10 ml of dry tetrahydrofuran were charged and the mixture was cooled to −78° C. To the mixture, the previously prepared reaction solution B was added. The reaction was continuously performed at −78° C. for 2 hours, followed by reaction at room temperature overnight. After the completion of the reaction, the solvent was distilled off and 40 ml of hexane was added to deposit a salt. The deposited salt was filtered and the filtrate was partially a concentrated and purified by distillation under reduced pressure to obtain 17.4 g of a pale yellow viscous liquid.

It was confirmed from the nuclear magnetic resonance absorption spectrum ($^1$H-NMR) and mass spectrum (FD-MS) that this liquid is N-(4-triethoxysilylphenyl)-N-phenyl-aminobenzene. Hereinafter, this is referred to as a surface-treating agent 3.

The oxidation potential of the resulting surface-treating agent 3 was measured by cyclic voltamogram. As a result, it was 1.13 V (reduced to oxidation potential on the basis of standard hydrogen electrode: 1.33 V, reduced to ionization potential: 5.83 eV).

Example 4

The surface-treating agent 1 (0.60 g) synthesized in Example 1 was charged in a Petri dish and 12.1 g of dry toluene distilled over metal sodium was added to dissolve the surface-treating agent. Furthermore, 0.8 g of triethylamine was added to form a treating-solution.

A glass substrate on which an ITO film(work function W=4.9 eV)was built up in a thickness of 40 nm according to a sputtering method was immersed in an aqueous neutral detergent solution diluted to 2%, and then washed by using an ultrasonic washer for 30 minutes. After washing, the detergent was washed away with running water of ultrahigh purity water for 5 minutes. Then, the washed glass substrate was immersed in acetone and washed by using an ultrasonic washer for 30 minutes. The acetone ultrasonic washing was repeated one more time. After drying with a nitrogen blow, the glass substrate was set to a plasma-treating device (PC-101A, manufactured by Yamato Kagaku Co.), followed by evacuation. After plasma-treating with oxygen for 30 minutes, the pressure was returned to atmospheric pressure and the glass substrate was taken out Immediately, the glass substrate was put in a gloved box wherein the atmosphere was replaced by dry nitrogen.

The above mentioned pretreated glass substrate with an ITO film was immersed in a treating-solution prepared in the gloved box wherein the atmosphere was replaced by dry nitrogen immediately after the pretreatment. After the 35 hours immersion, the glass substrate was taken out and then washed in toluene by using an ultrasonic washer for 30 minutes. Furthermore, it was subjected to ultrasonic washing using acetone in place of toluene for 30 minutes to remove an excess treating agent. After ultrasonic washing and further drying with a nitrogen blow, a surface-treated glass substrate with an ITO film was obtained.

A contact angle between the surface-treated glass substrate with an ITO film and water, and a contact angle between the non-surface-treated glass substrate with an ITO film and water were measured by using a contact angle measuring device (Model CA-A, manufactured by Kyowa Kaimen Kagaku Co., Ltd.). As a result, it was 80 degree and 10 degree, respectively. Accordingly, the ITO surface was hydrophobilized by the surface treatment. Furthermore, the composition analysis of the ITO surface was performed by using a X-ray photoelectronic spectroscopic analyzer (XPS) (SSX-100, manufactured by Surface Science Instrument Co.). The results are shown in Table 1. It was confirmed that the ITO surface was modified because the composition of Sn, In and O derived from ITO decreased while the composition of N, C and Si derived from the surface-treating agent increased.

TABLE 1

|  | In | Sn | 0 | C | Si | N |
|---|---|---|---|---|---|---|
| Surface treated | 20.0 | 0.6 | 37.5 | 37.5 | 2.9 | 1.4 |
| No surface treatment | 27.2 | 1.2 | 48.5 | 21.0 | 2.2 | 0 |

Unit: atomic %

Evaluation of Voltage-current Characteristics

On a surface-treated glass substrate with an ITO film, a polysilane thin film having a thickness of 600 nm was formed by using a 12% by weight toluene solution of poly(methylphenylsilane) synthesized in Reference Synthesis Example 1 according to a spin coating method. Then, aluminum as the cathode was deposited thereon in a thickness of 100 nm to fabricate a device for measuring voltage-current characteristics.

A voltage of 42 V (electric field: 0.7 MV/cm) was applied to this device for measuring voltage-current characteristics. As a result, a current having a current density of $2.1 \times 10^{-5}$ A/cm$^2$ flowed.

Furthermore, a peeling test using a Cellophane tape was performed. However, the polysilane thin film was not peeled from the glass substrate with an ITO film.

Comparative Example 1

According to the same manner as that described in Example 4 except that poly(methylphenylsilane) synthesized in Reference Synthesis Example 1 was used on a non-surface-treated glass substrate with an ITO film, which was pretreated (plasma treatment) but was not immersed in the surface-treating solution, a device for measuring

Example 5
Fabrication of Organic EL Device and its Evaluation

On a glass substrate with an ITO film, of which a surface was treated by using the surface-treating agent 1 synthesized in Example 1 in the same manner as that described in Example 4, a film as the hole transporting layer was formed in a thickness of 80 nm using a 2% by weight toluene solution of poly(methylphenylsilane) synthesized in Reference Synthesis Example 1 according to a spin coating method. After drying the film at 120° C. under reduced pressure for 1 hour, tris(8-quinolinol)aluminum ($Alq_3$) was deposited as the light emitting layer in a thickness of 50 nm on the hole transporting layer. Finally, an aluminum-lithium alloy [Al:Li=99:1 (weight ratio)] as the cathode was deposited in a thickness of 200 nm on the light emitting layer to fabricate an organic EL device having a two-layer structure. The vacuum degree on deposition was not more than $8 \times 10^{-6}$ Torr.

In this device Ip1(the ionization potential of the surface-treating agent 1), Ip2(the ionization potential of poly(methylphenylsilane)) and W(the work function of ITO) satisfied the formula $$W(=4.9\ eV) \leq Ip1(=5.47\ eV) \leq Ip2(=5.63\ eV).$$

A voltage of 11 V was applied to this organic EL device. As a result, a current having a current density of 4.4 $mA/cm^2$ flowed and emission of yellowish green EL light having a luminance of 138 $cd/m^2$ was observed. At this time, the electroluminescence efficiency (luminance/current density) was 3.2 cd/A. The EL peak wavelength was 520 nm and it nearly agreed with a fluorescent peak wavelength of an $Alq_3$ thin film.

Comparative Example 2
Fabrication of Organic EL Device and its Evaluation

According to the same manner as that described in Example 5 except that poly(methylphenylsilane) synthesized in Reference Synthesis Example 1 was used on a non-surface-treated glass substrate with an ITO film, which was pretreated (plasma treatment) in the same manner as that described in Example 4 but was not immersed in the surface-treating solution, an organic EL device having a two-layer structure, wherein a thickness of the hole transporting layer is 80 nm, was fabricated.

A voltage of 11 V was applied to this organic EL device. As a result, a current having a current density of 0.12 $mA/cm^2$ flowed and emission of yellowish green EL light having a luminance of 34 $cd/m^2$ was observed. At this time, the electroluminescence efficiency (luminance/current density) was 2.7 cd/A. The EL peak wavelength was 520 nm and it nearly agreed with a fluorescent peak wavelength of an $Alq_3$ thin film.

Example 6
Fabrication of Organic EL Device and its Evaluation

According to the same manner as that described in Example 4 except that poly(ethyl(4-(N,N-diphenylamino)phenyl)silane) synthesized in Reference Synthesis Example 2 was used on a glass substrate with an ITO film, of which a surface was treated by using the surface-treating agent 1 synthesized in Example 1 in the same manner as that described in Example 4, an organic EL device having a two-layer structure, wherein a thickness of the hole transporting layer is 80 nm, was fabricate.

A voltage of 11 V was applied to this organic EL device. As a result, a current having a current density of 29 $mA/cm^2$ flowed and emission of yellowish green EL light having a luminance of 760 $cd/m^2$ was observed. At this time, the electroluminescence efficiency (luminance/current density) was 2.7 cd/A. The EL peak wavelength was 520 nm and it nearly agreed with a fluorescent peak wavelength of an $Alq_3$ thin film.

Example 7
Fabrication of Organic EL Device and its Evaluation

On a glass substrate with an ITO film, of which a surface was treated by using the surface-treating agent 2 synthesized in Example 2 in the same manner as that described in Example 4, a film as the light emitting layer was formed in a thickness of 40 nm using a 1% by weight toluene solution of the light emitting polymer 1 synthesized in Reference Synthesis Example 3 according to a spin coating method. After drying the film at 120° C. under reduced pressure for 1 hour, tris(8-quinolinol)aluminum ($Alq_3$) was deposited as the electron transporting layer in a thickness of 50 nm on the light emitting layer. Finally, an aluminum-lithium alloy [Al:Li=99:1 (weight ratio)] as the cathode was deposited in a thickness of 200 nm on the electron transporting layer to produce an organic EL device having a two-layer structure. The vacuum degree on deposition was not more than $8 \times 10^{-6}$ Torr.

A voltage of 5 V was applied to this organic EL device. As a result, a current having a current density of 56 $mA/cm^2$ flowed and emission of yellowish green EL light having a luminance of 289 $cd/m^2$ was observed. At this time, the electroluminescence efficiency (luminance/current density) was 0.52 cd/A. The EL peak wavelength was 545 nm and it nearly agreed with a fluorescent peak wavelength of a thin film of the light emitting polymer 1. Furthermore, EL light emission from the light emitting polymer 1 was confirmed.

Example 8
Fabrication of Organic EL Device and its Evaluation

According to the same manner as that described in Example 7 except that light emitting polymer 1 synthesized in Reference Synthesis Example 3 was used on a glass substrate with an ITO film, of which a surface was treated by using the surface-treating agent 3 synthesized in Example 3 in the same manner as that described in Example 4, an organic EL device having a two-layer structure, wherein a thickness of the light emitting layer is 40 nm, was fabricated.

A voltage of 5 V was applied to this organic EL device. As a result, a current having a current density of 148 $mA/cm^2$ flowed and emission of yellowish green EL light having a luminance of 141 $cd/m^2$ was observed. At this time, the electroluminescence efficiency (luminance/current density) was 0.1 cd/A. The EL peak wavelength was 545 nm and it nearly agreed with a fluorescent peak wavelength of a thin film of the light emitting polymer 1. Furthermore, EL light emission from the light emitting polymer 1 was confirmed.

Example 9
Fabrication of Organic EL Device and its Evaluation

On a glass substrate with an ITO film, of which a surface was treated by using the surface-treating agent 2 synthesized in Example 2 in the same manner as that described in Example 4, a film as the hole transporting layer was formed in a thickness of 80 nm using a methylene chloride solution of poly(N-vinylcarbazole) (The oxidation potential: 1.20 V, reduced to oxidation potential on the basis of standard hydrogen electrode: 1.40 V, reduced to ionization potential: 5.90 eV)according to a dipping method. Furthermore, a film as the light emitting layer was formed in a thickness of 40 nm on the hole transporting layer using a toluene solution of the light emitting polymer 1 synthesized in Reference Synthesis Example 3 according to a spin coating method. After drying at 120° C. under reduced pressure for 1 hour, tris(8-quinolinol)aluminum ($Alq_3$) as the electron transporting layer was deposited in a thickness of 40 nm on the light emitting layer. Finally, an aluminum-lithium alloy [Al:Li= 99:1 (weight ratio)] as the cathode was deposited in a thickness of 140 nm on the electron transporting layer to fabricate an organic EL device having a three-layer structure. The vacuum degree on deposition was not more than $8 \times 10^{-6}$ Torr.

A voltage of 7 V was applied to this organic EL device. As a result, a current having a current density of 22.9 $mA/cm^2$ flowed and emission of yellowish green EL light having a luminance of 804 $cd/m^2$ was observed.

Comparative Example 3

According to the same manner as that described in Example 9 except for using a non-surface-treated glass substrate with in ITO film, which was pretreated (plasma treatment) in the same manner as that described in Example 4 but was not immersed in the surface-treating solution, a three-layer structure organic EL device comprising poly(N-vinylcarbazole) as the hole transporting layer, the light emitting polymer 1 as the light emitting layer and tris(8-quinolilol)aluminum ($Alq_3$) as the electron transporting layer was fabricated.

A voltage of 7 V was applied to this organic EL device. As a result, a current having a current density of 0.5 $MA/cm^2$ flowed and emission of yellowish green EL light having a luminance of 23 $cd/m^2$ was observed.

Reference Synthesis Example 4

In a flask, 5 g of 1-bromopyrene (manufactured by Tokyo Kasei Co.) and 50 ml of dry tetrahydrofuran were charged and the mixture was cooled to −78° C. 11.7 ml of a 1.6 M n-butyllithium/hexane solution was added dropwise and, after the completion of the dropwise addition, the reaction was continuously performed for 1 hour. The resulting reaction solution is referred to as a reaction solution C.

In another flask, 7.2 g of chlorotriethoxysilane and 50 ml of dry tetrahydrofuran were charged and the mixture was cooled to −78° C. To the mixture, the previously prepared reaction solution C was added. The reaction was continuously performed at −78° C. for 1 hour, followed by reaction at room temperature overnight. After the completion of the reaction, the solvent was distilled off. An operation of adding dry toluene and distilling off the solvent was repeated to remove excess chlorotriethoxysilane. Dry toluene was added to deposit a salt. The deposited salt was filtered and the filtrate was concentrated to obtain 4.97 g of a viscous liquid.

It was confirmed from $^1$H-NMR Spectrum and FD-MS Spectrum that this liquid is 1-(triethoxysilyl)-pyrene. Hereinafter, this is referred to as a surface-treating agent 4.

The oxidation potential of the resulting surface-treating agent 4 was measured by cyclic voltamogram. As a result, it was 0.87 V (reduced to oxidation potential on the basis of standard hydrogen electrode: 1.07 V, reduced to ionization potential: 5.57 eV).

Example 10

According to the same manner as that described in Example 4, a glass substrate with an ITO film was surface-treated with the surface-treating agent 4 synthesized in Reference Synthesis Example 4. A contact angle between the glass substrate with an ITO film and water was measured by using the above mentioned contact angle measuring device. As a result, it was 44 degree. In case of a non-surface-treated glass substrate with an ITO film, it was 8 degree. Accordingly, the ITO surface was hydrophobilized by the surface treatment.

On the surface-treated glass substrate with an ITO film, a film as the light emitting layer was formed in a thickness of 40 nm using a toluene solution of the light emitting polymer 1 synthesized in Reference Synthesis Example 3 according to a spin coating method. After drying at 120° C. under reduced pressure for 1 hour, tris(8-quinolinol)aluminum ($Alq_3$) as the electron transporting layer was deposited in a thickness of 40 nm on the light emitting layer. Finally, an aluminum-lithium alloy [Al:Li=99:1 (weight ratio)] as the cathode was deposited in a thickness of 140 nm on the light emitting layer to fabricate an organic EL device having a two-layer structure. The vacuum degree on deposition was not more than $8 \times 10^{-6}$ Torr.

This device was continuously driven at a given current density of 25 $mA/cm^2$. The luminance after aging for 7 hours was 250 $cd/m^2$. The luminance after aging for 250 hours was 118 $cd/m^2$. Furthermore, a rate of an increase in voltage during driving after aging for 7 hours was 0.005 V/hour.

Comparative Example 4

According to the same manner as that described in Example 10 except for using a non-surface-treated glass substrate with an ITO film, which was pretreated (plasma treatment) in the same manner as that described in Example 4 but was not immersed in the surface-treating solution, a two-layer structure organic EL device comprising the light emitting polymer 1 as the light emitting layer and tris(8-quinolinol)aluminum ($Alq_3$) as the electron transporting layer was fabricated.

This device was continuously driven at a given current density of 25 $mA/cm^2$. The luminance after aging for 7 hours was 194 $cd/m^2$. The luminance after aging for 250 hours was 75 $cd/m^2$. Furthermore, a rate of an increase in voltage during driving after aging for 7 hours was 0.006 V/hour.

The silicon-containing compound of the present invention is superior in effect of improving the mechanical and electric contact and adhesion between an electrode (e.g. transparent conductive electrode, etc.) and an organic layer, and is suitably used as a surface-treating agent having the hole transporting property. Furthermore, an organic electroluminescence device using the same is industrially useful because the mechanical and electric contact and adhesion between the electrode and organic layer are improved.

What is claimed is:

1. A silicon-containing compound having an oxidation potential of 0.3 to 1.5 V on the basis of a standard hydrogen electrode, wherein the structural formula of the silicon-containing compound is represented by the general formula (1):

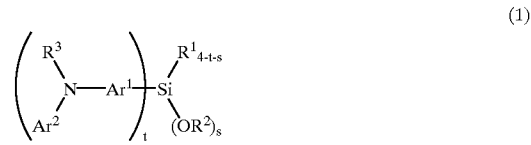

wherein $R^1$ represents a hydrogen atom, or a straight-chain or branched alkyl group having 1 to 10 carbon atoms, a cycloalkyl group having 10 carbon atoms or less, an aryl group having 6 to 24 carbon atoms or an aralkyl group having 7 to 26 carbon atoms; $R^2$ represents a straight-chain or branched alkyl group having 1 to 10 carbon atoms, $R^3$ represents an aryl group having 6 to 24 carbon atoms; $Ar^1$ represents an arylene group having 6 to 24 carbon atoms; $Ar^2$ represents an aryl group having 6 to 24 carbon atoms or the general formula (2):

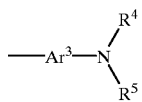

(2)

wherein $Ar^3$ represents an arylene group having 6 to 24 carbon atoms; and $R^4$ and $R^5$ independently represent a straight-chain or branched alkyl group having 1 to 10 carbon atoms, a cycloalkyl group having 10 carbon atoms or less, an aryl group having 6 to 24 carbon atoms or an aralkyl group having 7 to 26 carbon atoms; s and t independently represent an integer from 1 to 3, which satisfy the expression $2 \leq s + t \leq 4$; and a ring may be independently formed between $Ar^1$ and $Ar^2$, or alternatively a ring may be independently formed between $R^4$ and $Ar^3$, or $R^4$ and $R^5$ when $Ar^2$ is represented by the general formula (2).

2. The silicon-containing compound according to claim 1, wherein $R^3$ in the general formula (1) represents a phenyl group, $Ar^1$ represents a phenylene group, $Ar^2$ represents a phenyl group, or when $Ar^2$ is represented by the general formula (2), $R^4$ and $R^5$ independently represent a phenyl group and $Ar^3$ represents a phenylene group or a biphenylene group.

3. A surface-treating agent of an electrode, comprising the silicon-containing compound of claim 1 having an oxidation potential of 0.3 to 1.5 V on the basis of a standard hydrogen electrode, wherein at least one alkoxy group is bonded to a silicon atom and at least one aromatic amine group is also bonded to the silicon atom.

4. A surface-treating agent of an electrode, comprising the silicon-containing compound of claim 1 or 3.

5. A surface-treating agent of an electrode, comprising a silicon-containing compound which has an oxidation potential of 0.3 to 1.5 V on the basis of a standard hydrogen electrode, and is represented by the following general formula (3):

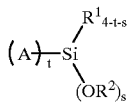

(3)

wherein $R^1$, $R^2$, s and t are the same as those defined in the general formula (1); and A represents a condensed polycyclic aromatic group having 14 to 30 carbon atoms.

6. A silicon-containing compound according to claim 1, wherein $R^1$ represents a member selected from the group consisting of methyl, ethyl, n-propyl, isopropyl, n-butyl, sec-butyl, tert-butyl, pentyl, hexyl, octyl, dodecyl, phenyl, naphthyl, anthryl, biphenyl, benzyl, phenethyl or p-methylbenzyl.

7. A silicon-containing compound according to claim 1, wherein $R^1$ represents methyl, ethyl, n-propyl, iso-propyl or n-butyl.

8. A silicon-containing compound according to claim 1, wherein $R^2$ represents a member selected from the group consisting of ethyl, n-propyl, iso-propyl, n-butyl, sec-butyl, tert-butyl, pentyl, hexyl, octyl and dodecyl.

9. A silicon-containing compound according to claim 1, wherein $R^2$ represents methyl or ethyl.

10. A silicon-containing compound according to claim 1, wherein $R^3$ represents a member selected from the group consisting of methyl, ethyl, n-propyl, iso-propyl, n-butyl, sec-butyl, tert-butyl, pentyl, hexyl, octyl, dodecyl, cyclohexyl, phenyl, naphthyl, anthryl, biphenyl, benzyl, phenethyl and p-methylbenzyl.

11. A silicon-containing compound according to claim 1, wherein $Ar^2$ is an aryl group selected from the group consisting of phenyl, naphthyl anthryl and biphenyl.

12. A silicon-containing compound according to claim 1, wherein $R^4$ and $R^5$ independently represent a member selected from the group consisting of methyl, ethyl, n-propyl, iso-propyl, n-butyl, sec-butyl, tert-butyl, pentyl, hexyl, octyl, dodecyl, cyclohexyl, phenyl, naphthyl, anthryl, biphenyl, benzyl, phenethyl and p-methylbenzyl.

13. A silicon-containing compound according to claim 1, wherein $Ar^3$ represents an arylene group selected from the group consisting of phenylene, naphthylene and biphenylene.

14. A method of preparing a silicon-containing compound according to claim 1, said method comprising:

halogenating a compound represented by the Formula (a):

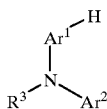

(a)

at a temperature within the range of from −20° C. to 150° C. with a halogenating agent to obtain a halogenated amine compound represented by the Formula (b):

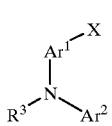

(b)

wherein said Formula (a) and said Formula (b) $Ar^1$, $R^3$ and $Ar^2$ are as defined in claim 1 and X represents a halogen atom;

lithiating a compound represented by Formula (b) with an organo lithium reagent to obtain a lithium compound represented by Formula (e)

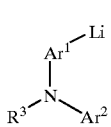

(e)

wherein said lithiation the organo lithium reagent is added at a temperature of from −80° C. to 0° C.;

allowing the lithium compound represented by Formula (e) to react with an alkoxy silane compound represented by the Formula (g)

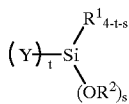

(g)

wherein Y represents halogen atom or an alkoxy group, said reaction being conducted at a temperature of from −80° C. to 0° C. whereby the compound represented by Formula (1) in claim 1 is obtained.

15. A method of preparing a silicon-containing compound according to claim 1, said method comprising:

halogenating a compound represented by the Formula (a):

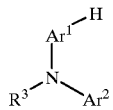

(a)

at a temperature within the range of from −20° C. to 150° C. with a halogenating agent to obtain a halogenated amine compound represented by the Formula (b)

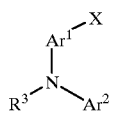

(b)

wherein said Formula (a) and said Formula (b) $Ar^1$, $R^3$ and $Ar^2$ are as defined in claim 1 and X represents a halogen atom;

subjecting a compound represented by Formula (b) to a Grignard reaction by allowing the compound represented by Formula (b) to react with a metal magnesium reagent to obtain a Grignard compound represented by Formula (f)

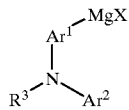

(f)

wherein the reaction is conducted at a temperature of from −0° C. to 150° C.;

allowing the Grignard compound represented by Formula (f) to react with an alkyl silane compound represented by the Formula (g)

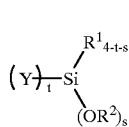

(g)

wherein Y represents halogen atom or an alkoxy group, said reaction being conducted at a temperature of from −80° C. to 0° C. whereby the compound represented by Formula (1) in claim 1 is obtained.

16. A method according to claim 14, wherein said lithiation reagent is represented by the formula Li $R^{17}$ wherein $R^{17}$ is alkyl.

17. A method according to claim 14 or 15, wherein said halogenating agent is n-bromosuccinimide, bromine, or pyridinium hydrobromide perbromide.

* * * * *